United States Patent
Okada et al.

(10) Patent No.: US 11,028,131 B2
(45) Date of Patent: Jun. 8, 2021

(54) MUTANT OF ADENO-ASSOCIATED VIRUS (AAV) CAPSID PROTEIN

(71) Applicants: NIPPON MEDICAL SCHOOL FOUNDATION, Tokyo (JP); NATIONAL CENTER OF NEUROLOGY AND PSYCHIATRY, Tokyo (JP); TAKARA BIO INC., Shiga (JP)

(72) Inventors: Takashi Okada, Tokyo (JP); Hironori Okada, Tokyo (JP); Hiromi Kinoh, Tokyo (JP); Tatsuji Enoki, Kusatsu (JP); Toshikazu Nishie, Kusatsu (JP); Junichi Mineno, Kusatsu (JP)

(73) Assignees: NIPPON MEDICAL SCHOOL FOUNDATION, Tokyo (JP); NATIONAL CENTER OF NEUROLOGY AND PSYCHIATRY, Tokyo (JP); TAKARA BIO INC., Shiga (JP)

(*) Notice: Subject to any disclaimer, the term of this patent is extended or adjusted under 35 U.S.C. 154(b) by 0 days.

(21) Appl. No.: 16/481,159

(22) PCT Filed: Jan. 29, 2018

(86) PCT No.: PCT/JP2018/002680
§ 371 (c)(1),
(2) Date: Jul. 26, 2019

(87) PCT Pub. No.: WO2018/139634
PCT Pub. Date: Aug. 2, 2018

(65) Prior Publication Data
US 2020/0002384 A1     Jan. 2, 2020

(30) Foreign Application Priority Data
Jan. 30, 2017     (JP)  .............................. JP2017-014377

(51) Int. Cl.
*C12N 7/00* (2006.01)
*C12N 15/00* (2006.01)
(Continued)

(52) U.S. Cl.
CPC .............. *C07K 14/005* (2013.01); *C12N 7/00* (2013.01); *C12N 15/85* (2013.01);
(Continued)

(58) Field of Classification Search
None
See application file for complete search history.

(56) References Cited

U.S. PATENT DOCUMENTS

| 9,938,541 B2 | 4/2018 | Nishie et al. |
| 2005/0053922 A1 | 3/2005 | Schaffer et al. |

(Continued)

FOREIGN PATENT DOCUMENTS

| JP | 2007-527219 | 9/2007 |
| WO | 2004/112727 | 12/2004 |

(Continued)

OTHER PUBLICATIONS

Gao et al., "Clades of Adeno-Associated Viruses Are Widely Disseminated in Human Tissues," Journal of Virology, vol. 78, No. 12: 6381-6388 (Year: 2004).*

(Continued)

*Primary Examiner* — M Franco G Salvoza
(74) *Attorney, Agent, or Firm* — Wenderoth, Lind & Ponack, L.L.P.

(57) ABSTRACT

The present invention provides: a mutant of adeno-associated virus (AAV) capsid protein, which contains at least one amino acid substitution in PLA2 domain when compared with the amino acid sequence for wild-type AAV capsid protein; a nucleic acid encoding the mutant; a cell containing the nucleic acid; a method for producing a recombinant AAV (Continued)

1: brain
2: heart
3: muscle
4: AAV2 (positive control)
5: Ad5 (negative control)
M: Marker particle, comprising a step of culturing the cell to produce the recombinant AAV particle; a recombinant AAV particle containing the mutant; a composition containing the recombinant AAV particle; and a method for transferring a gene into a target cell, comprising a step of bringing the recombinant AAV particle into contact with the target cell.

6 Claims, 1 Drawing Sheet

Specification includes a Sequence Listing.

(51) Int. Cl.
 *C07K 14/005* (2006.01)
 *C12N 15/85* (2006.01)
(52) U.S. Cl.
 CPC ............... *C12N 2750/14121* (2013.01); *C12N 2750/14122* (2013.01); *C12N 2750/14123* (2013.01); *C12N 2750/14151* (2013.01)

(56) References Cited

U.S. PATENT DOCUMENTS

| | | | |
|---|---|---|---|
| 2005/0255089 A1 | 11/2005 | Chiorini | |
| 2009/0202490 A1* | 8/2009 | Schaffer | C07K 14/005 424/93.2 |
| 2013/0096182 A1* | 4/2013 | Chatterjee | C07K 14/00 514/44 A |
| 2015/0315610 A1 | 11/2015 | Nishie et al. | |

FOREIGN PATENT DOCUMENTS

| | | |
|---|---|---|
| WO | 2005/005610 | 1/2005 |
| WO | 2008/124724 | 10/2008 |
| WO | 2014/103957 | 7/2014 |
| WO | 2014/194132 | 12/2014 |
| WO | 2017/066764 | 4/2017 |

OTHER PUBLICATIONS

GenBank: AAS99309.1 from Gao et al. (Year: 2004).*
NCBI Blast Alignment for GenBank: AAS99309.1 and instant SEQ ID No. 6 (Year: 2020).*
Lucchese et al., "How a single amino acid change may alter the immunological information of a peptide," Frontiers in Bioscience, E4 : 1843-1852 (Year: 2012).*
L. Vandenberghe et al., "Efficient Serotype-Dependent Release of Functional Vector into the Culture Medium During Adeno-Associated Virus Manufacturing", Human Gene Therapy, vol. 21, Oct. 2010, pp. 1251-1257.
S. Kronenberg et al., "A Conformational Change in the Adeno-Associated Virus Type 2 Capsid Leads to the Exposure of Hidden VP1 N Termini", Journal of Virology (American Society for Microbiology), May 2005, vol. 79, No. 9, pp. 5296-5303.
P. Wu et al., "Mutational Analysis of the Adeno-Associated Virus Type 2 (AAV2) Capsid Gene and Construction of AAV2 Vectors with Altered Tropism", Journal of Virology (American Society for Microbiology), Sep. 2000, vol. 74, No. 18, pp. 8635-8647.
N. Maheshri et al., "Directed evolution of adeno-associated virus yields enhanced gene delivery vectors", Nature Biotechnology, Feb. 2006, vol. 24, No. 2, pp. 198-204.
J. Johnson et al., "Mutagenesis of Adeno-Associated Virus Type 2 Capsid Protein VP1 Uncovers New Roles for Basic Amino Acids in Trafficking and Cell-Specific Transduction", Journal of Virology (American Society for Microbiology), Sep. 2010, vol. 84. No. 17, pp. 8888-8902.
L. Zhong et al., "Next generation of adeno-associated virus 2 vectors: Point mutations in tyrosines lead to high-efficiency transduction at lower doses", Proceedings of the National Academy of Sciences, USA, Jun. 3, 2008, vol. 105, No. 22, pp. 7827-7832.
Search Report dated Apr. 24, 2018, in International (PCT) Application No. PCT/JP2018/002680.
International Preliminary Report on Patentability dated Jul. 30, 2019, in International (PCT) Application No. PCT/JP2018/002680.
Extended European Search Report dated Oct. 14, 2020 in corresponding European Patent Application No. 18744464.1.

* cited by examiner

[FIG. 1]
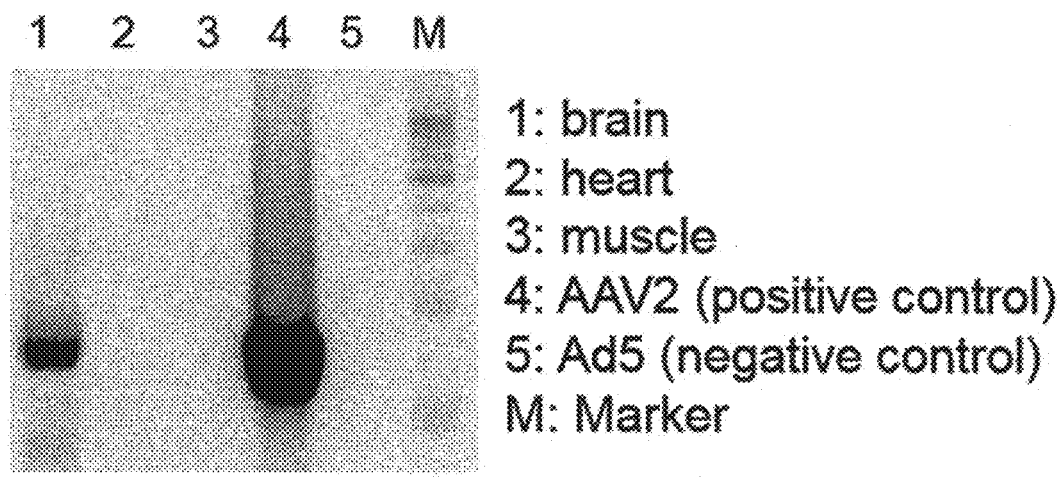
1: brain
2: heart
3: muscle
4: AAV2 (positive control)
5: Ad5 (negative control)
M: Marker
[FIG. 2]
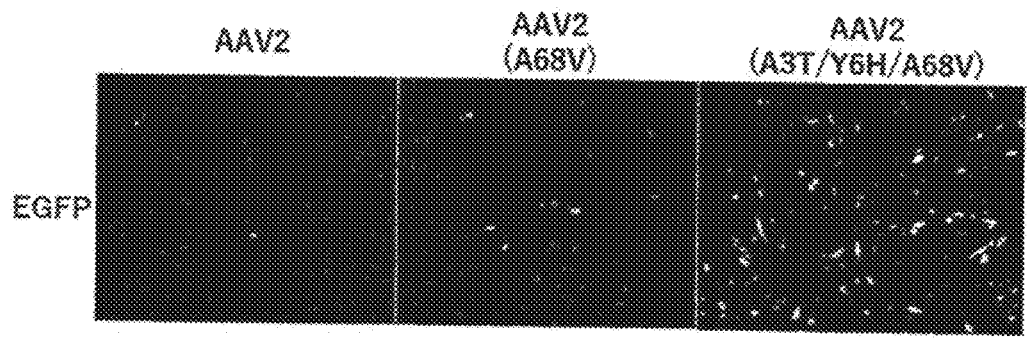

MUTANT OF ADENO-ASSOCIATED VIRUS (AAV) CAPSID PROTEIN

TECHNICAL FIELD

The present invention relates to mutants of adeno-associated virus (AAV) capsid protein. The AAV capsid protein mutants of the present invention are particularly useful for gene transfer into a target cell and/or expression of the transgene in the target cell.

BACKGROUND ART

Adeno-associated virus (AAV) is a non-enveloped virus with a diameter of about 20 nm which infects mammals such as humans and primates, and is classified into family Parvoviridae, genus Dependovirus. TO date, a large number of AAV serotypes have been identified (for example, Non-Patent Literature 1), and it is known that different serotypes of AAV infect different types of animals or cells.

The AAV genome is a single stranded DNA (ssDNA) of approximately 4.7 kb, and comprises inverted terminal repeat (ITR) sequences of about 145 bases at both ends. The ITR sequence forms Watson-Crick base pairs by itself to form a T-type hairpin structure comprising cis elements necessary for replication and packaging of the AAV genome. The AAV genome comprises two open reading frames (ORFs) in a region flanked by the ITR sequences. One ORF (also called "rep gene") encodes four Rep proteins (Rep78, Rep68, Rep52 and Rep40). The other ORF (also called "cap gene") encodes three capsid proteins (VP1, VP2 and VP3) and an assembly-activating protein (AAP). The Rep proteins have helicase activity, and are required not only for induction of outer shell formation but also for integration of the AAV genome into a host cell chromosome. On the other hand, a total of 60 molecules of VP1, VP2 and VP3 assemble at a ratio of 1:1:10 to form an icosahedral AAV outer shell. VP1, VP2 and VP3 are mainly different in the N-terminal region. For example, a phospholipase A2 (phospholipase A2: PLA2) domain is present at the N-terminus of VP1. Since the PLA2 domain is present only in VP1, the N-terminal region of VP1 is also called a VP1 unique region (VP1u). The PLA2 domain is known to be exposed to outside of the AAV particle under acidic conditions, though it is usually present inside the AAV particle. Thus it is believed that the PLA2 domain is necessary for AAV to escape from endosome and transfer into a nucleus after the AAV enters a cell (Non-patent Literature 2). AAP is a protein necessary for formation of AAV capsid.

Replication of AAV in nature depends on the presence of a helper virus such as adenovirus and herpes virus. In the presence of a helper virus, the AAV genome is replicated in a host cell and a complete AAV particle containing the AAV genome is formed. Then, the AAV particle is released from the host cell. In the absence of a helper virus, the AAV genome is episomally maintained, or is integrated into a host chromosome and becomes latent.

AAV can infect a wide variety of cells including human cells, and AAV infects even non-dividing cells in which differentiation terminates, including blood cells, muscle cells, and nerve cells. In addition, since AAV is not pathogenic to human, it has a low risk of adverse effect. The virus particle of AAV is physicochemically stable. For these reasons, AAV has recently attracted attention to utility value as a vector for gene transfer used in gene therapy for the treatment of congenital genetic disease as well as the treatment of cancer or infection.

Production of genetically modified AAV (hereinafter, referred to as recombinant AAV) is usually performed by introducing elements essential for formation of an AAV particle in the form of a nucleic acid construct(s) into a cell to produce a cell having the ability to produce the virus (hereinafter, referred to as a virus-producing cell), and culturing the cell to express the elements essential for AAV particle formation. In general, of the elements essential for AAV particle formation, the elements that need to be provided in cis and the elements that can be provided in trans are separately introduced into a cell as separate constructs, thereby production of a wild-type AAV and self-replication of a recombinant AAV in a host are prevented.

Generally, the virus-producing cell is produced by introducing three types of plasmids as described below into a cell. 1) A plasmid for supplying a recombinant AAV genome which retains ITR sequences at both ends, from which rep and cap genes are removed, and which carries a desired heterologous polynucleotide (sometimes referred to as a transgene) in place of the removed rep and cap genes (hereinafter, referred to as a vector plasmid); 2) a plasmid for supplying Rep proteins and capsid proteins (hereinafter, referred to as a packaging plasmid); and 3) a plasmid for supplying only elements' essential for AAV particle formation among adenovirus-derived elements (hereinafter, referred to as a helper plasmid).

Using a recombinant AAV particle loaded with a desired heterologous polynucleotide enables long-term stable gene transfer into various target cells or target organs. To date, it has been shown that gene transfer into skeletal muscle cells, liver cells (liver), cardiomyocytes (heart), nerve cells, pancreatic gland cells, and pancreatic islet cells is possible. Furthermore, a recombinant AAV has been used in human clinical trials.

On the other hand, attempts to change the cell tropism of AAV (Patent Literature 1) or to increase gene transfer efficiency (for example, Patent Literature 2 and Patent Literature 3) were made by altering capsid proteins. For example, Patent Literature 2 discloses that long-term survival of AAV in a living body becomes possible by replacing an antigenic residue present on the outer shell surface of AAV with another amino acid to avoid removal of AAV particles by a neutralizing antibody, and as a result, the gene transfer efficiency is increased. Patent Literature 3 discloses that long-term survival of AAV in a living body becomes possible by replacing, a tyrosine residue present on the outer shell surface of AAV with another amino acid (for example, phenylalanine) to inhibit ubiquitination of tyrosine in a cell and avoid ubiquitin-proteasome hydrolysis, and as a result, the gene transfer efficiency is increased.

CITATION LIST

Patent Literatures

Patent Literature 1: WO 2014/103957
Patent Literature 2: WO 2014/194132
Patent Literature 3: WO 2008/124724

Non-Patent Literatures

Non-Patent Literature 1: Vandenberghe et al., Human Gene Therapy, Vol. 21, pp. 1251-1257, 2010
Non-Patent Literature 2: Kronenberghe et al., Journal of Virology, Vol. 79, pp. 5296-5303, 2005

SUMMARY OF THE INVENTION

Technical Problems

As described above, attempts to increase gene transfer efficiency by altering AAV capsid proteins have ever been made. However, such attempts to increase gene transfer efficiency and/or gene expression efficiency by using a recombinant AAV still have room for improvement. Specifically, infection of a target cell with AAV and expression of a transgene are accomplished by passing through plural steps. Thus it is expected that the gene transfer efficiency and/or the gene expression efficiency can be synergistically increased by improving each step.

An object of the present invention is to provide mutants of AAV capsid proteins in order to increase the efficiency of gene transfer into a target cell and/or to increase the efficiency of gene expression by using a recombinant AAV.

Solutions to the Problems

As a result of intensive efforts to solve the above-described problems, the present inventors found that desired gene can be introduced into a target cell with high efficiency and the gene can be strongly expressed in the cell by utilizing a novel mutant of an AAV capsid protein. Thus the present invention was completed.

Specifically, the present invention relates to:

[1] a mutant of an adeno-associated virus (AAV) capsid protein, comprising one or more amino acid replacements in a PLA2 domain as compared with the amino acid sequence of a wild-type AAV capsid protein,
wherein the one or more amino acid replacements are located at one or more positions selected from the group consisting of:
(1) alanine at position 3,
(2) tyrosine at position 6,
(3) alanine at position 68,
(4) aspartic acid at position 87,
(5) leucine at position 91,
(6) serine at position 149,
(7) proline at position 150, and
(8) serine at position 156
in the amino acid sequence of AAV2 VP1 capsid protein, or at one or more positions corresponding to the above (1) to (8) in the amino acid sequence of VP1 capsid protein of an AAV other than AAV2;

[2] the mutant of an AAV capsid protein according to [1], wherein the one or more amino acid replacements are one or more amino acid replacements selected from the group consisting of:
(1) a replacement of alanine at position 3 by threonine (A3T),
(2) a replacement of tyrosine at position 6 by histidine (Y6H),
(3) a replacement of alanine at position 68 by valine (A68V),
(4) a replacement of aspartic acid at position 87 by asparagine (D87N),
(5) a replacement of leucine at position 91 by proline (L91P),
(6) a replacement of serine at position 149 by tyrosine (S149Y),
(7) a replacement of proline at position 150 by histidine (P150H), and
(8) a replacement of serine at position 156 by tyrosine (S156Y)
in the amino acid sequence of AAV2 VP1 capsid protein, or one or more amino acid replacements corresponding to the above (1) to (8) in the amino acid sequence of VP1 capsid protein of an AAV other than AAV2;

[3] the mutant of an AAV capsid protein according to [1], wherein the one or more amino acid replacements are one or more amino acid replacements selected from the group consisting of:
(1) a replacement of alanine at position 3 by threonine (A3T),
(2) a replacement of tyrosine at position 6 by histidine (Y6H), and
(3) a replacement of alanine at position 68 by valine (A68V)
in the amino acid sequence of AAV2 VP1 capsid protein, or one or more amino acid replacements corresponding to the above (1) to (3) in the amino acid sequence of VP1 capsid protein of an AAV other than AAV2;

[4] the mutant according to anyone of [1] to [3], which is a mutant of AAV2 capsid protein;

[5] a nucleic acid encoding the mutant of an AAV capsid protein according to any one of [1]-[4];

[6] a cell containing the nucleic acid according to [5];

[7] a method of producing a recombinant AAV particle, the method comprising a step of culturing the cell according to [6] to produce a recombinant AAV particle;

[8] the method of producing a recombinant AAV particle according to [7], wherein the cell according to [6] further contains a nucleic acid encoding an AAV Rep protein, a nucleic acid encoding an adenovirus-derived element necessary for formation of an AAV particle, and a nucleic acid having a nucleotide sequence of an AAV genomic DNA;

[9] a recombinant AAV particle containing the mutant of an AAV capsid protein according to any one of [1]-[4];

[10] a composition containing the recombinant AAV particle according to [9]; and

[11] a method of introducing a gene into a target cell, the method comprising a step of bringing the recombinant AAV particle according to [9] into contact with a target cell.

Effects of the Invention

According to the present invention, a gene transfer system useful for gene transfer into a target cell is provided. The recombinant AAV particle of the present invention can introduce a gene into a target cell with high efficiency, allow the gene introduced into the target cell to be transcribed with high efficiency, and then allow the gene to be strongly expressed.

BRIEF DESCRIPTION OF DRAWINGS

FIG. 1 shows results of electrophoresis in Example 1.
FIG. 2 shows results of fluorescence microscope observation in Example 3.

DESCRIPTION OF EMBODIMENTS

As used herein, the term "adeno-associated virus (AAV)" refers to small virus that infects primates and other mammals including humans and is classified into family Parvoviridae, genus Dependovirus. AAV has a non-enveloped icosahedral outer shell and a single-stranded genomic DNA within the shell. As used herein, if not otherwise specified, AAV includes wild-type virus and its derivatives, and also includes all serotypes and clades. As used herein, the serotype of an AAV particle is based on the serotype from which capsid is derived. In other words, the serotype of a recombinant AAV particle is determined based on the source of cap gene used for preparation of the recombinant AAV particle, and does not depend on the serotype of an AAV genome encapsulated in the recombinant AAV particle. For example, when capsid protein is derived from AAV6 and ITR sequences in an AAV genome encapsulated in a recombinant AAV particle are derived from AAV2, the recombinant AAV particle is defined as serotype 6.

As used herein, the term "capsid protein" means a protein which is encoded by cap gene present in a viral genome and constitutes the outer shell of virus. The wild-type AAV genome or cap gene encodes three capsid proteins (VP1, VP2 and VP3). As used herein, all of VP1, VP2 and VP3 are included in the capsid protein.

As used herein, the term "AAV particle" means a particle having a complete outer shell structure. An AAV genome may or may not be contained within the outer shell. In other words, as used herein, the AAV particle also includes an AAV particle containing a recombinant AAV genome (sometimes referred to as an AAV vector) and an AAV-like particle that does not contain an AAV genome (for example, an AAV hollow particle: NO 2012/144446).

As used herein, the term "recombinant" means production using genetic recombination technology. For example, a recombinant AAV particle means an AAV particle produced using genetic recombination technology, and a recombinant DNA means a DNA produced using genetic recombination technology.

As used herein, the term "wild-type." means the type most commonly found in a wild population among species. In contrast to a mutant-type, the wild-type refers to a phenotype that is considered basic or an individual having the phenotype. The wild-type is also called "normal-type". On the other hand, as used herein, the term "mutant" means a protein, virus, cell, individual or the like expressing a change in trait caused by a mutated gene. Furthermore, as used herein, the term "mutant" may also refer to the mutated gene itself.

As used herein, the term "amino acid replacement" means a replacement of an amino acid in a protein molecule by another amino acid due to non-synonymous mutation. The amino acid replacement may be naturally occurring due to differences between species or individuals, or may be artificially induced. The artificial induction may be performed by a known method. For example, a polypeptide comprising an amino acid sequence having one or several amino acid replacements can be produced by introducing a base replacement, deletion, addition or insertion into a nucleic acid encoding the polypeptide by a known method.

The present invention is explained in detail below.

(I) AAV Capsid Protein Mutant

The mutant of an AAV capsid protein of the present invention is produced by replacing at least one amino acid with another amino acid in the amino acid sequence of an AAV capsid protein. Use of the AAV capsid protein mutant enables introduction of a gene into a target cell with high efficiency and strong expression of the gene in the cell.

The serotype or origin of the AAV capsid protein that can be used in the present invention is not particularly limited, and may be any known serotype or origin. Examples of the AAV capsid proteins that can be used in the present invention include, but are not limited to, capsid proteins of any AAV including AAV from primates such as AAV type 1 (AAV1), AAV type 2 (AAV2), AAV type 3 (AAV3a and AAV3b), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), AAV type 12 (AAV12), and AAV type 13 (AAV13), and AAV from non-primate animals such as avian AAV, bovine AAV, canine AAV, equine AAV, ovine AAV, and goat AAV. In addition, AAV capsid proteins derived from any known serotype AAV or capsid proteins of any known recombinant AAV can be also used in the present invention. For example, the amino acid replacement as identified by the present invention can be introduced simultaneously with a mutation known to increase gene transfer efficiency and/or gene expression efficiency into an AAV capsid protein to synergistically increase the gene transfer efficiency and/or gene expression efficiency of AAV having the capsid protein. Furthermore, the present invention may be combined with a known mutation that changes stability or cell tropism. In the present invention, AAV2 capsid protein can be preferably used. The amino acid sequence of wild-type AAV2 VP1 is shown in SEQ ID NO: 2.

A person skilled in the art can easily identify a position in the amino acid sequence of an capsid protein of an AAV serotype or clade other than AAV2 corresponding to each amino acid position in the amino acid sequence of AAV2 capsid protein. See, for example, amino acid sequence alignments of VP1 described in Gao et al., Proc. Natl. Acad. Sci. USA, Vol. 99, No. 18, pp. 11854-11859, 2002.

The amino acid replacement in the AAV capsid protein mutant of the present invention occurs in a position selected from (1) alanine at position 3, (2) tyrosine at position 6, (3) alanine at position 68, (4) aspartic acid at position 87, (5) leucine at position 91, (6) serine at position 149, (7) proline at position 150, and (8) serine at position 156 in the amino acid sequence of wild-type AAV2 VP1 capsid protein, or in a position selected from positions corresponding to the above (1) to (8) in the amino acid sequence of VP1 capsid protein of AAV other than AAV2. As used herein, the term "AAV other than AAV2" means AAV of a serotype or clade other than AAV2, and examples thereof include, but not limited to, AAV1, AAV3 (AAV3a and AAV3b), AAV4, AAV5, AAV6, AAV7, AAV8, AAV9, AAV10, AAV11, AAV12, and AAV13, and AAV from non-primate animals such as avian AAV, bovine AAV, canine AAV, equine AAV, ovine AAV, and goat AAV. As used herein, the phrase "a position(s) corresponding to" or "one or more positions corresponding to" means, in the case where the AAV capsid protein mutant of the present invention is an AAV2 capsid protein mutant, the amino acid position(s) represented by the above (1) to (8), and in the case where the AAV capsid protein mutant of the present invention is a mutant of capsid protein of AAV of a serotype or clade other than AAV2, a position(s) corresponding to the above (1) to (8) in the amino acid sequence of VP1 capsid protein of AAV of the serotype or clade. Such corresponding positions in the amino acid sequence of VP1 capsid protein of an AAV serotype or clade other than AAV2 are easily determined by a person skilled in the art as described above.

The positions of the amino acid replacements all are present in the PLA2 domain. The PLA2 domain is present in VP1 but not in VP2 and VP3. In other words, the capsid protein that can be used in the present invention is preferably a protein containing a PLA2 domain, such as VP1. Examples of the protein containing a PLA2 domain include, but not limited to, a full-length VP1, a VP1 fragment, a PLA2 domain, and a fusion protein of a PLA2 domain and another protein.

In the AAV capsid protein mutant of the present invention, an amino acid residue after the amino acid replacement is not particularly limited as long as the desired function is obtained. The amino acid residue after the amino acid replacement may be a natural amino acid or an artificial amino acid as long as the desired function is obtained. There are 20 amino acids in nature except for some special amino acids. The natural amino acids are classified into several groups based on their structures. Examples of the groups include, but not limited to, group A: glycine, alanine; group B: valine, leucine, isoleucine; group C: aspartic acid, glutamic acid; group D: asparagine, glutamine; group E: serine, threonine; group F: lysine, arginine, histidine; group G: phenylalanine, tyrosine, tryptophan; group H: cysteine, methionine; and group I: proline. Since amino acid residues contained in the same group have similar property, it is expected that they are mutually exchangeable.

Examples of the amino acid replacement include, but not limited to, (1) a replacement of alanine at position 3 by threonine (A3T), (2) a replacement of tyrosine at position 6 by histidine (Y6H), (3) a replacement of alanine at position 68 by valine (A68V), (4) a replacement of aspartic acid at position 87 by asparagine substitution (D87N), (5) a replacement of leucine at position 91 by proline (L91P), (6) a replacement of serine at position 149 by tyrosine (S149Y), (7) a replacement of proline at position 150 by histidine (P150H), and (8) a replacement of serine at position 156 by tyrosine (S156Y) in the amino acid sequence of AAV2 VP1 capsid protein, and, amino acid replacements corresponding to the above (1) to (8) in the amino acid sequence of VP1 capsid protein of AAV other than AAV2. As used herein, the phrase "an amino acid replacement(s) corresponding to" or "one or more amino acid replacements corresponding to" means, in the case where the AAV capsid protein mutant of the present invention is an AAV2 capsid protein mutant, the amino acid replacement(s) represented by the above (1) to (8), and in the case where the AAV capsid protein mutant of the present invention is a mutant of a capsid protein of an AAV serotype or clade other than AAV2, the corresponding amino acid replacements that occur in positions corresponding to the amino acid positions represented by the above (1) to (8) in the amino acid sequence of VP1 capsid protein of the AAV serotype or clade. As described above, the corresponding amino acid positions in the amino acid sequence of VP1 capsid protein of an AAV serotype or clade other than AAV2 are easily determined by a person skilled in the art.

Preferable examples of the amino acid replacements include one or more amino acid replacements selected from the group consisting of (1) a replacement of alanine at position 3 by threonine (A3T), (2) a replacement of tyrosine at position 6 by histidine (Y6H), and (3) a replacement of alanine at position 68 by valine (A68V) in the amino acid sequence of AAV2 VP1 capsid protein, and one or more amino acid replacements selected from the group consisting of amino acid replacements corresponding to the above (1) to (3) in the amino acid sequence of VP1 capsid protein of an AAV other than AAV2.

More preferable examples of the amino acid replacements are three amino acid replacements consisting of (1) a replacement of alanine at position 3 by threonine (A3T), (2) a replacement of tyrosine at position 6 by histidine (Y6H), and (3) a replacement of alanine at position 68 by valine (A68V) in the amino acid sequence of AAV2 VP1 capsid protein, or three amino acid replacements consisting of amino acid replacements corresponding to the above (1) to (3) in the amino acid sequence of VP1 capsid protein of an AAV other than AAV2. For example, a protein represented by SEQ ID NO: 6, which is obtained by introducing the three amino acid replacements (A3T/Y6H/A68V) into the VP1 of wild-type AAV2, is an example of the present invention.

(II) Nucleic Acid Encoding AAV Capsid Protein Mutant

The present invention provides a nucleic acid encoding a mutant of an AAV capsid protein. The nucleic acid of the present invention encodes the mutant of an AAV capsid protein as described in above (I). The nucleic acid of the present invention is produced by replacing at least one base in the nucleotide sequence of a nucleic acid (cap gene) encoding an AAV capsid protein with another base.

The nucleic acid of the present invention may be present in the form of DNA, or may be in the form of RNA or a chimera of DNA and RNA. The nucleic acid of the present invention also includes a complementary nucleic acid (for example, cDNA). The nucleic acid of the present invention may be single-stranded or double-stranded. The nucleic acid of the present invention is preferably double-stranded.

The serotype or origin of the cap gene of AAV that can be used in the present invention is not particularly limited, and may be any known serotype or origin. Examples of the AAV serotype that can be used in the present invention include, but not limited to, any AAV such as AAV type 1 (AAV1), AAV type 2 (AAV2), AAV type 3 (AAV3a and AAV3b), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), AAV type 12 (AAV12), and AAV type 13 (AAV13), avian. AAV, bovine AAV, canine AAV, equine AAV, ovine AAV, and goat AAV. In addition, a cap gene derived from any known serotype AAV or a cap gene of any known recombinant AAV can be also used in the present invention. In the present invention, AAV2 cap gene can be preferably used. The nucleotide sequence of wild-type AAV2 cap gene (nucleotide sequence encoding VP1) is shown in SEQ ID NO: 1.

Examples of the nucleic acid encoding a mutant of an AAV capsid protein include, but not limited to, a nucleic acid encoding AAV2 VP1 (A68V) (SEQ ID NO: 3), and a nucleic acid encoding AAV2 VP1 (A3T/Y6H/A68V) (SEQ ID NO: 5).

The nucleic acid of the present invention may be operably linked to an appropriate regulatory sequence. Examples of the regulatory sequence include a promoter sequence, a polyadenylation signal, a transcription termination sequence, an upstream regulatory domain, an internal ribosome entry site (IRES), and an enhancer. Examples of the promoter sequence include an inducible promoter sequence, and a constitutive promoter sequence. The regulatory sequence may be inherent in or foreign to the AAV from which the capsid protein is derived, and may be a natural sequence or a synthetic sequence. A recombinant DNA comprising the nucleic acid of the present invention which is capable of expressing an AAV capsid protein mutant is also included in the present invention.

The recombinant DNA is useful for delivering the nucleic acid of the present invention to cells in vitro, ex vivo or in vivo to impart ability to express the AAV capsid protein mutant to the cells. The cell to which the nucleic acid of the present invention has been delivered is useful for production of a recombinant AAV particle. The recombinant DNA can be used particularly for delivery or introduction of the nucleic acid of the present invention to eukaryotic cells, preferably animal cells, more preferably mammalian cells.

In the present invention, a DNA used as a vector is loaded with the nucleic acid of the present invention to produce a recombinant DNA. For example, a plasmid, a phage, a transposon, a cosmid, an episomal DNA, a viral genome or the like can be used.

For example, a plasmid can be loaded with the nucleic acid (cap gene) encoding the AAV capsid protein mutant of the present invention to produce a packaging plasmid. The packaging plasmid may further contain any nucleotide sequence such as a nucleic acid encoding a Rep protein (a rep gene).

A recombinant DNA comprising the nucleic acid of the present invention can be also produced by replacing at least one base in the PLA2 domain-encoding region in the nucleotide sequence of a cap gene loaded into a known packaging plasmid with another base. Examples of the packaging plasmid include, but not limited to, a packaging plasmid loaded with a cap gene, preferably a packaging plasmid loaded with a cap gene and a rep gene. An example of the packaging plasmid loaded with a cap gene and a rep gene is pAAV-Ad-ACG2 (SEQ ID NO: 7).

Introduction of a base replacement into a nucleic acid may be performed by a known method, and for example, it is achieved by performing PCR using a commercially available reagent such as Mutagenesis Basal Kit (manufactured by TAKARA BIO INC.) following instructions attached to the kit.

(III) Cell Containing the Nucleic Acid of the Present Invention

The present invention also provides a cell, for example an isolated cell, containing the nucleic acid of the present invention, specifically the recombinant DNA as described in above (II). The isolated cell is, for example, a cell line maintained in vitro. The cell of the present invention is useful for production of the recombinant AAV particle of the present invention as explained below. When the cell of the present invention is used to produce a viral particle, the cell is referred to as "a virus-producing cell" (also referred to as a packaging cell or a producer cell). The recombinant DNA of the present invention as described in above (II) may be integrated into the genome of the cell of the present invention, or may be retained within the cell so as to transiently express the AAV capsid protein mutant.

Examples of a method for introducing a recombinant DNA (nucleic acid construct) containing the nucleic acid of the present invention into a cell include transient or constitutive introduction methods. Examples of a transient introduction method include, but not limited to, any known transient introduction methods, such as a calcium phosphate method, a lipofection method, a DEAE dextran method, a polyethyleneimine method, and an electroporation method. A commercially available reagent, for example, TransIT (registered trademark)-293 Reagent (manufacture by Mirus Bio LLC), TransIT (registered trademark)-2020 (manufacture by Mirus Bio LLC), Lipofectamine (registered trademark) 2000 Reagent (manufactured by Thermo Fisher Scientific Inc.), Lipofectamine (registered trademark) 2000CD Reagent (manufactured by Thermo Fisher Scientific Inc.), or FuGene (registered trademark) Transfection Reagent (manufactured by Promega Corporation) may be used. Baculovirus can also be used to introduce a nucleic acid construct into an insect cell.

Examples of a constitutive introduction method include, but not limited to, any known constitutive introduction methods, such as a method comprising use of a retrovirus vector, and a method comprising introducing a plasmid by a transient introduction method as described above and selecting cells in which a recombinant DNA is integrated into the chromosomes of the cells. In the method comprising use of a retrovirus vector, a commercially available reagent such as Retorovirus Constructive System (manufactured by TAKARA BIO INC.) may be used.

The recombinant DNA of the present invention is stably or transiently introduced into cells by using such established techniques. For stable transformation, a selection marker, for example, a well-known selection marker such as a neomycin resistance gene (encoding neomycin phosphotransferase) or a hygromycin B resistance gene (encoding aminoglycoside phosphotransferase) can be linked with the recombinant DNA of the present invention.

As a cell into which the nucleic acid of the present invention is introduced, various eukaryotic cells such as mammalian cells including rodent cells and primate cells (for example, human cells), and insect cells can be used.

The cell into which the nucleic acid of the present invention is introduced may be a primary cultured cell or a cell line. Examples of a suitable cell line include a 293 cell (ATCC CRL-1573), a 293T cell, a 293F cell, a 293FT cell, a 293EB cell, a COS cell, a HeLa cell, a Vero cell, a 3T3 mouse fibroblast, a C3H10T1/2 fibroblast, a CHO cell, a Sf9 cell (ATCC CRL-1711), a AAV 293 cell (manufactured by Stratagene), and cells derived from these cells. In the present invention, for example, preferably used is a cell modified so as to transiently or constitutively express one or some of proteins necessary for production of a recombinant AAV, such as the 293 cell or the like which constitutively expresses adenovirus E1 protein.

(IV) Recombinant AAV Particle and Method of Producing Recombinant AAV Particle

The recombinant AAV particle of the present invention is a recombinant AAV particle comprising a mutant of an AAV capsid protein. The recombinant AAV particle can be produced from the cell as described in above (III). The recombinant AAV particle of the present invention is useful for introduction of a gene into a target cell. The gene introduced by the recombinant AAV particle of the present invention is strongly expressed in the target cell.

The recombinant AAV particle can be produced using a cell containing several elements necessary for production of AAV particles as a virus-producing cell. The first element is a "recombinant AAV genome" to be replicated in cells and packaged in AAV particles. The recombinant AAV genome comprises a desired heterologous polynucleotide and two inverted terminal repeat (ITR) sequences located on either side, i.e. 5'-side and 3'-side of the desired heterologous polynucleotide. The desired heterologous polynucleotide may have a gene that is desired to be expressed in a cell infected with the recombinant AAV particle, and a regulatory sequence for the expression. The nucleotide sequence of the ITR sequence is known. For example, for ITR sequences derived from AAV2, see Kotin R. M. et al., Human Gene Therapy, volume 5, pages 793-801, 1994. ITR sequences derived from any of various AAV serotypes, such as AAV1, AAV2, AAV3, AAV4, AAV5, and AAV7, can be used. The ITR sequences used in the present invention may be sequences derived from a wild-type AAV or may be sequences altered by insertion, deletion or replacement of a nucleotide(s). The ITR sequences allow replication of the recombinant AAV genome in the presence of Rep protein and allow packaging of the recombinant AAV genome into a capsid particle during AAV particle formation.

The desired heterologous polynucleotide with which the recombinant AAV genome can be loaded generally has a size of less than about 5 kilobases (kb). The recombinant AAV genome can be loaded with a heterologous nucleotide depending on the purpose, for example a gene encoding a desired protein which has been deleted or lost in a recipient, a gene encoding a protein having a desired biological or therapeutic activity (for example, antibacterial, antiviral or antitumor activity), a desired nucleotide sequence encoding an RNA that inhibits or reduces the production of a harmful or undesired protein, a nucleotide sequence encoding an antigenic protein, or a gene encoding a marker protein (for example, EGFP, luciferase, LacZ).

In an aspect of the present invention, the recombinant AAV genome lacks the cap gene region and/or the rep gene region. In this aspect, when AAV particles in which the recombinant AAV genome has been packaged infect cells, the AAV particles do not replicate alone in the infected cells.

For example, a plasmid may be used to introduce the first element (recombinant AAV genome) into cells. When the first element is introduced into cells by a plasmid, the plasmid is referred to as a vector plasmid.

The second element necessary for necessary for production of AAV particles is a "nucleic acid construct that provides packaging function". The nucleic acid construct encodes a gene derived from AAV that provides a protein necessary for formation of AAV particles. In other words, the nucleic acid construct contains the rep gene region or the cap gene region or both, which are major ORFs of AAV. In order to produce the recombinant AAV particle, of the present invention, the nucleic acid encoding the AAV capsid protein mutant of the present invention is used as the cap gene. The virus-producing cell as described in above (III) which has the ability to express the above-described mutant can be used for production of AAV particles. The outer shell of AAV particles is formed by assembling many molecules of capsid proteins VP1, VP2 and VP3. In the recombinant AAV particle of the present invention, all molecules of capsid protein VP1 may be the mutants, or a part of molecules of capsid protein VP1 constituting the outer shell of the AAV particle may be the mutants and the rest may be the wild-type capsid protein VP1. Furthermore, capsid proteins VP2 and VP3 constituting the outer shell of the recombinant AAV particle of the present invention may also have mutations. The capsid protein mutants contained in the recombinant AAV particle of the present invention may be a single type of mutants or plural types of mutants.

The AAV rep gene encodes four Rep proteins (Rep 78, Rep 68, Rep 52 and Rep 40). These Rep proteins are shown to have many functions, for example recognition, binding and nicking of DNA replication origin of an AAV genome, DNA helicase activity, and alteration of transcription by an AAV-derived promoter.

For example, a plasmid may be used to introduce the second element (a nucleic acid construct that provides packaging function) into cells. When the second element is introduced into cells by a plasmid, the plasmid is referred to as a packaging plasmid.

The third element necessary for production of AAV particles is a "helper virus function (also called accessory function)" for AAV replication. For introduction of the helper virus function, a virus or a nucleic acid construct can be used. When a virus is used, though adenovirus is generally used, a virus such as herpes simplex virus type 1 or 2 or vaccinia virus can also be used. When a virus is used, the cells into which the first element and the second element have been introduced are infected with the virus as a helper virus. Because packaging of AAV particles only requires expression of adenovirus early genes, for example, an adenovirus that does not express late genes may be used. An adenovirus mutant that is deficient in late gene expression (for example, ts100K or ts149 adenovirus mutant) can be used. When a nucleic acid construct is used, a nucleic acid construct that provides the helper virus function is prepared from a nucleic acid necessary for the helper virus function which is isolated from a helper virus, and then introduced into the cells. The nucleic acid construct that provides the helper virus function comprises a nucleotide sequence for providing one or more kinds of helper virus function, and is provided to the cells in the form of a plasmid, phage, transposon, cosmid or another virus.

For example, a plasmid may be used to introduce the third element (helper virus function) into cells. When the third element is introduced into cells by a plasmid, the plasmid is referred to as a helper plasmid. A commercially available helper plasmid, for example, pHelper Vector (manufactured by TAKARA BIO INC.) may be used.

For production of AAV particles, 1) a step of introducing the first element, i.e. the recombinant AAV genome, into cells, 2) a step of introducing the second element, i.e. the nucleic acid construct that provides packaging function, into cells, and 3) a step of introducing the third element, i.e. the helper virus function, into cells are performed. These steps may be performed simultaneously or sequentially. The steps 1) to 3) may be performed in any order. Virus-producing cells thus produced are cultured. In the virus-producing cells, the recombinant AAV genome is excised by the expression product of the rep gene and then replicated. The expressed capsid proteins form an outer shell, and the recombinant AAV genome is packaged in the outer shell to produce AAV particles. When the virus-producing cell expresses a mutant of an AAV capsid protein, the outer shell of the produced AAV particle contains the mutant of the AAV capsid protein. The cells into which the first to third elements are introduced are the same as the "cells into which the nucleic acid of the present invention is introduced" described in above (III).

Culturing of the virus-producing cells can be performed under known culture conditions. Examples of the culture conditions include, but not limited to, a temperature of 30 to 40° C., preferably 37° C., a humidity of 90 to 99%, preferably 95%, and $CO_2$ concentration of 2 to 10%, preferably $CO_2$ concentration of 5%. Temperature, humidity and $CO_2$ concentration lying out of the above-mentioned ranges may be used as long as growth of the virus-producing cells and production of the recombinant AAV are achieved. Culture time is not particularly limited, and examples thereof include 12 to 150 hours, preferably 48 to 120 hours. A medium used for culturing the virus-producing cells may contain components necessary for cell culture. Examples of the medium include basal synthetic media such as DMEM, IMDM, and DMEM:F-12, the basal synthetic media additionally containing, if necessary, fetal bovine serum, growth factors and peptides, and the basal synthetic media containing an increasing amounts of amino acids.

The recombinant AAV particles formed in the virus-producing cells remain in the cells or are released into a culture supernatant. It is known that the abundance ratio of recombinant AAV particles in virus-producing cells to those in the culture supernatant differs depending on AAV serotypes (Adachi et al., Gene Therapy and Regulation, Vol. 5, pp. 31-55, 2010). For purifying the recombinant AAV particles from the virus-producing cells, a sample containing the recombinant AAV particles is prepared by disrupting the cells using a known method or by bringing the cells into contact with an acidic solution (WO 2015/005430). The sample thus prepared is subjected to a purification step. On the other hand, for purifying the recombinant AAV particles from the culture supernatant, the culture supernatant may be directly subjected to a purification step, or may be concentrated and then subjected to a purification step. The culture supernatant may be concentrated by a known method, or by using a commercially available reagent such as AAVpro (registered trademark) Concentrator (manufactured by TAKARA BIO INC.).

Examples of a purification method of AAV particles include, but not limited to, various purification methods such as CsCl gradient ultracentrifugation, chromatography, and ultrafiltration. The AAV particles can be isolated and purified from a sample containing the recombinant AAV particles by appropriately using the above-described purification methods. The AAV particles can also, be purified by using commercially available reagents, such as AAVpro (registered trademark) Purification Kit (All Serotypes) (manufactured by TAKARA BIO INC.).

When a helper virus is used in above step 3) (a step of introducing the third element, i.e. the helper virus function, into cells), for example, a step of separating the AAV particles and the helper virus based on size may be added. The AAV particles can also be separated from the helper virus based on differences in affinity for heparin. Furthermore, the remaining helper virus can be inactivated using a known method. For example, adenovirus can be inactivated by heating at about 60° C., for example for 20 minutes or more. This treatment is effective for selective removal of adenovirus used as a helper virus because AAV particles are extremely stable to heat.

The amount of the recombinant AAV particles is shown as the titer of the recombinant AAV particles or the like. The titer of the recombinant AAV particles is shown as, but not limited to, in a certain amount of a sample, (a) the number of AAV genomes (genomic titer), (b) the infection ability (infectious titer) of AAV to cells as determined experimentally, or (c) the amount (or purity) of protein constituting AAV.

Examples of a method for determining above (a) include a method comprising determination of the copy number (genome copy: g.c.) of the AAV genome in a sample containing the AAV particles by PCR. For the determination of genomic titer, for example, AAVpro (registered trademark) Titration Kit (for Real Time PCR) Ver. 2 (manufactured by TAKARA BIO INC.) is used, and the genomic titer can be calculated by a method as described in the attached, instruction manual. Examples of a method for determination of above (b) include a method comprising infection of a suitable target cell with serially diluted solutions of a sample containing the AAV particles and detection of change in the form of the cell (cytopathy), a method comprising detection of the expression of a transgene, and a method comprising determination of the copy number of the AAV genome introduced into the cell. Examples of a method for determination of above (c) include a method comprising SDS-PAGE analysis of the protein and a method comprising quantitative determination of the protein by an immunological technique.

(V) Method for Introduction of Gene Into Target Cell Comprising Step of Contacting Recombinant AAV Particle With Target Cell The purified recombinant AAV particles of the present invention are used for delivery of a desired heterologous polynucleotide to a target cell, for the purpose of gene therapy and other purposes. In general, the AAV particles introduce a desired gene into a target cell in vivo or in vitro. For in vitro gene introduction, the AAV particles are brought into contact with cells obtained from a living organism. The cells can also be transplanted into a living body. For transplantation of the cells into a living body, the cells are formulated as a pharmaceutical composition, and various techniques such as intramuscular, intravenous, subcutaneous and intraperitoneal administration can be used. For in vivo gene introduction, the AAV particles are formulated as a pharmaceutical composition, and the pharmaceutical composition is generally administered parenterally (for example, administered via an administration route such as intramuscularly, subcutaneously, intratumorally, transdermally, intrathecally, etc.). The pharmaceutical composition comprising the AAV particles contains a pharmaceutically acceptable carrier and optionally other agents, such as a pharmaceutical, stabilizer, a buffer, a carrier, an adjuvant, and a diluent.

As the target cell, for example, various eukaryotic cells such as mammalian cells including rodent cells and Primate cells (for example, human cells) and insect cells can be used. The target cell may be a primary cultured cell or a cell line. Examples thereof include, but not limited to, a CHO cell, and preferably a CHO-K1 cell.

As used herein, the term "gene transfer efficiency" means a proportion of the number of cells that have acquired the AAV genome in the number of cells subjected to gene introduction. Moreover, it is possible to estimate the gene transfer efficiency on the basis of the degree of introduction of the desired heterologous nucleotide per target cell, that is, the copy number of the AAV genome per cell. The introduced AAV genome may be integrated into the chromosomes of the target cells or maintained episomally. When the recombinant AAV particle of the present invention is used, it is possible to achieve gene transfer efficiency equal to or higher than that achieved by using a conventional recombinant AAV particle.

As used herein, the term "gene expression efficiency" means the degree of expression of the desired heterologous nucleotide per target cell. Even when the amount of a transcript (mRNA) is measured instead of the amount of an expression product (protein), the term "gene expression efficiency" is used herein. When the recombinant AAV particle of the present invention is used, it is possible to achieve gene transfer efficiency at least 2 times, at least 3 times, at least 4 times, at least 5 times or at least 10 times that achieved by using a conventional recombinant AAV particle.

EXAMPLES

The present invention will be more specifically explained by Examples described below, to which the scope of the present invention should not be limited.

Example 1 Isolation of Marmoset AAV

A genomic DNA was collected from the brain, heart and skeletal muscle of an aged common marmoset (10 years-old or older, died of debilitation). Then, 293EB cells were transfected with the genomic DNA, pAd5 (manufactured by Agilent Technologies Inc.), pSV3neo-LargeT and pE1Δ55 (WO2012/144446), and then cultured. The cells were collected, and a cell lysate was prepared. Then, 293 cells were transfected with the lysate and adenovirus type 5 (Ad5), and then cultured. The cells were collected, and a cell lysate was prepared. Using the lysate as a template, a primer set designed for a highly conserved region of AAV, and Tks Gflex (trademark) DNA polymerase (manufactured by TAKARA BIO INC.), PCR was performed for 50 cycles of 10 seconds at 98° C. and 15 seconds at 61° C. When PCR amplified products were loaded on an agarose gel and electrophoresed, a band of an amplified product corresponding to AAV was found in a sample derived from the 293EB cells transfected with the brain-derived genomic DNA (FIG. 1). A DNA fragment extracted from the band was cloned, and its nucleotide sequence was determined. As a result, several marmoset AAV clones were obtained.

Example 2 Comparison of Marmoset AAV with AAV2

When the amino acid sequence of VP1 of marmoset AAV that was determined in Example 1 was compared with the amino acid sequence of VP1 of AAV2 (SEQ ID NO: 2), different amino acids were found at 11 positions (A3T, Y6H, A68V, D87N, L91P, S149Y, P150H, S156Y, Y444F, Y500F, Y730F).

Among them, the amino acid residues at 8 positions on the N-terminal side (threonine at position 3, histidine at position 6, valine at position 68, asparagine at position 87, proline at position 91, tyrosine at position 149, histidine at position 150, tyrosine at position 156) have never been found in other AAV serotypes and are all located in a VP1 unique region (VP1u).

On the other hand, the amino acid residues at 3 positions on the C-terminal side (phenylalanine at position 444, position 500 and position 730) have been known in other AAV serotypes, and are located in a common region of VP1, VP2 and VP3.

Example 3 Preparation of AAV2 Mutant

Mutations were introduced into the cap gene of AAV2 to prepare two AAV2 mutants in which a portion of the amino acid sequence of VP1 was replaced with an amino acid sequence derived from VP1 of marmoset AAV, i.e. AAV2 (A68V) and AAV2(A3T/Y6H/A68V). For VP1 of each AAV2 mutant, the nucleotide sequences of cap gene encoding the VP1 and the amino acid sequences of the full length VP1 are shown in Table 1.

TABLE 1

| | Nucleotide sequence | Amino acid sequence |
|---|---|---|
| AAV2 VP1, (A68V) | SEQ ID NO: 3 | SEQ ID NO: 4 |
| AAV2 VP1 (A3T/Y6H/A68V) | SEQ ID NO: 5 | SEQ ID NO: 6 |

The viral genomes of these AAV2 mutants are loaded with an EGFP gene. Cells infected with the AAV2 mutants can express EGFP. A method for producing the AAV2 mutants is shown below.

(1) Preparation of Packaging Plasmid Mutant

Packaging plasmid pAAV-Ad-ACG2 (SEQ ID NO: 7) contains the rep gene of AAV2 and the cap gene of AAV2. A packaging plasmid mutant, pAAV-Ad-ACG2(A68V), was produced by performing PCR using pAAV-Ad-ACG2 as a template, a mutant-1F primer (SEQ ID NO: 8), a mutant-1R primer (SEQ ID NO: 9), and PrimeSTAR (registered trademark) Mutagenesis Basal Kit (manufactured by TAKARA BIO INC.) following instructions attached to the kit. The cap gene present on this mutant plasmid contains the nucleotide sequence shown by SEQ ID NO: 3 in the VP1 coding region. Similarly, pAAV-Ad-ACG2(A3T/Y6H/A68V) was produced by performing PCR using the above-described pAAV-Ad-ACG2(A68V) as a template, a mutant-2F primer (SEQ ID NO: 10) and mutant-2R primer (SEQ ID NO: 11). The cap gene present on this mutant plasmid contains the nucleotide sequence shown by SEQ ID NO: 5 in the VP1 coding region.

(2) Introduction of Plasmid into 293EB Cell

Each packaging plasmid mutant prepared in Example 3-(1), a helper plasmid (pHelper Vector, manufactured by TAKARA BIO INC.) and a vector plasmid (pAAV-CB-EGFP, SEQ ID NO: 12) were introduced into 293EB cells by a transfection method using polyethylenimine (manufactured by Cosmo Bio Inc.). The 293EB cells were cultured in a DMEM medium containing 1/100 volume of GlutaMax (manufactured by Gibco) at 37° C. and 5% $CO_2$ for 3 days.

(3) Purification of AAV2 Mutant

The AAV2 mutants were purified from the 293EB cells cultured as described in Example 3-(2) and a culture supernatant. From the 293EB cells, the AAV2 mutants were purified by using AAVpro (registered trademark) Purification Kit (All Serotypes) (manufactured by TAKARA BIO INC.) following instructions attached to the kit. From the culture supernatant, the AAV2 mutants were purified by using AAVpro (registered trademark) Concentrator (manufactured by TAKARA BIO INC.) following instructions attached to the kit. The AAV2 mutant purified from the 293EB cells and the AAV2 mutant purified from the culture supernatant were mixed and used for the next experiments. These two AAV2 mutants are designated AAV2(A68V) and AAV2(A3T/Y6H/A68V)

(4) Titer determination of AAV2 Mutant

The AAV2 mutant solution obtained in Example 3-(3) (5 µL), phosphate buffered saline (PBS) (84.5 µL), 20 mM $MgCl_2$ (10 µL), and 250 U/µL Benzonase (0.5 µL) were mixed, and incubated at room temperature for 1 hour to degrade free genomic DNAs and plasmid DNAs. After 100 µL of PBS was added, the genomic DNA of AAV was purified by using DNeasy Blood & Tissue Kit (manufactured by Qiagen) following instructions attached to the kit. Using this AAV genomic DNA as a template, an ITR-F primer (SEQ ID NO: 13), an ITR-R primer (SEQ ID NO: 14), and SYBR (registered trademark) Premix DimerEraser (trademark) (Perfect Real Time) (manufactured by TAKARA BIO INC.), quantitative PCR was performed following instructions attached to the kit. On the other hand, as a standard, quantitative PCR was performed under the same conditions as described above except that the vector plasmid linearized by digestion with restriction enzyme SacI was used, and then a standard curve was prepared. Thus, genomic titer of the AAV2 mutants obtained in Example 3-(3) was determined.

Example 4 Infection with AAV2 Mutant

With $5 \times 10^5$ g.c./cells of each AAV2 mutant obtained in Example 3-(3), CHO-K1 cells ($2 \times 10^4$ cells) were infected (n=3). As a control, CHO-K1 cells were infected with the wild-type AAV2 under the same conditions. These CHO-K1 cells were cultured on a collagen-coated 96-well plate at 37° C. and 5% $CO_2$ for 48 hours, and then the expression of EGFP was observed with a fluorescence microscope (FIG. 2).

Lysis Buffer (manufactured by Thermo Fisher Scientific Inc.) was added to the CHO-K1 cells at 100 µl/well and then incubated at 75° C. for 10 minutes to extract a mixture of DNA and RNA. The mixture of DNA and RNA was stored at −80° C. until use. Then, three experiments as below were performed.

First, quantitative PCR was performed using the DNA in the mixture as a template, a hamster-actin-F primer (SEQ ID NO: 15), a hamster-actin-R primer (SEQ ID NO: 16), and SYBR (registered trademark) Premix Ex Taq (trademark) (Tli RNase H Plus) (manufactured by TAKARA BIO INC.). The PCR was performed following instructions attached to the kit. From an experimental result, the number of cells in each well (cell) was determined. Next, quantitative PCR was performed using the DNA in the mixture as a template, an ITR-F primer (SEQ ID NO: 13), an ITR-R primer (SEQ ID NO: 14), and SYBR (registered trademark) Premix DimerEraser (trademark) (Perfect Real Time) (manufactured by TAKARA BIO. INC.). The PCR was performed following instructions attached to the kit. From an experimental result, the number of genome copies of AAV present in each well (genome copy: g.c.) was determined. Based on these values, the number of AAV genome copies per cell (g.c./cell) was calculated.

Furthermore, quantitative RT-PCR was performed using the RNA in the mixture as a template, High-Capacity cDNA Reverse Transcription Kit (manufactured by Thermo Fisher Scientific Inc.), an EGFP-F primer (SEQ ID NO: 17) and an EGFP-R primer (SEQ ID NO: 18). The RT-PCR was performed following instructions attached to the kit. From an experimental result, the transcription amount of the EGFP gene in each well (EGFP) was determined. Based on the transcription amount of EGFP (EGFP) and the number of cells (cell), the EGFP transcription amount per cell (EGFP/cell) was calculated.

Based on the number of AAV genome copies pet cell (g.c./cell) and the EGFP transcription amount per cell (EGFP/cell), the EGFP transcription amount per genome copy (EGFP/g.c.) was calculated. Results are shown relatively to results of the wild-type AAV2 in Table 2.

TABLE 2

|  | g.c./cell | EGFP/cell | EGFP/g.c. |
|---|---|---|---|
| AAV2 | 1 | 1 | 1 |
| AAV2 (A68V) | 1.7 | 4.3 | 2.5 |
| AAV2 (A3T/Y6H/A68V) | 1.1 | 18.0 | 16.8 | g.c. = genome copy

As for the number of AAV genome copies per cell (g.c./cell), each AAV2 mutant showed a value not more than 2 times that of the wild-type AAV2, and there was not a large difference. This result suggests that the infection efficiency and gene transfer efficiency of AAV do not differ much between the wild-type AAV2 and the AAV2 mutants.

As for the EGFP transcription amount per cell (EGFP/cell) and the EGFP transcription amount per genome copy (EGFP/g.c.), however, both of AAV2(A68V) and AAV2 (A3T/Y6H/A68V) showed high values as compared with the wild-type AAV2. Particularly, AAV2(A3T/Y6H/A68V) showed very high values, wherein the EGFP transcription amount per cell (EGFP/cell) and the EGFP transcription amount per genome copy (EGFP/g.c.) were 18.0 times and 16.8 times higher than the EGFP/cell and EGFP/g.c. of the wild-type AAV2, respectively. These results show that the efficiency of transcription from the gene introduced into the target cell is high, and thus the transcription amount of the foreign gene per cell is also high. In other words, it is suggested that a foreign gene can be efficiently transcribed and expressed in a target cell by using, for example, AAV2 (A3T/Y6H/A68V).

INDUSTRIAL APPLICABILITY

According to the present invention, mutants of adeno-associated virus (AAV) capsid proteins are provided. The AAV capsid protein mutants of the present invention are particularly useful for introduction of a gene into a target cell and/or expression of the transgene in the target cell.

SEQUENCE LISTING FREE TEXT

SEQ ID NO: 1: a nucleotide sequence encoding AAV2 VP1
SEQ ID NO: 2: an amino acid sequence of AAV2 VP1
SEQ ID NO: 3: a nucleotide sequence encoding AAV2 VP1 (A68V)
SEQ ID NO: 4: an amino acid sequence of AAV2 VP1 (A68V)
SEQ ID NO: 5: a nucleotide sequence encoding AAV2 VP1 (A3T/Y6H/A68V)
SEQ ID NO: 6: an amino acid sequence of AAV2 VP1 (A3T/Y6H/A68V)
SEQ ID NO: 7: a nucleotide sequence of pAAV-Ad-ACG2
SEQ ID NO: 8: a nucleotide sequence of mutant-1F primer
SEQ ID NO: 9: a nucleotide sequence of mutant-1R primer
SEQ ID NO: 10: a nucleotide sequence of mutant-2F primer
SEQ ID NO: 11: a nucleotide sequence of mutant-2R primer
SEQ ID NO: 12: a nucleotide sequence of pAAV-CB-EGFP
SEQ ID NO: 13: a nucleotide sequence of ITR-F primer
SEQ ID NO: 14: a nucleotide sequence of ITR-R primer
SEQ ID NO: 15: a nucleotide sequence of hamster-actin-F primer
SEQ ID NO: 16: a nucleotide sequence of hamster-actin-R primer
SEQ ID NO: 17: a nucleotide sequence of EGFP-F primer
SEQ ID NO: 18: a nucleotide sequence of EGFP-R primer

---

The invention claimed is:

1. A mutant of an adeno-associated virus (AAV) capsid protein, comprising one or more amino acid replacements in a PLA2 domain as compared with the amino acid sequence of a wild-type AAV capsid protein,
   wherein the one or more amino acid replacements comprise an amino acid replacement of alanine at position 68 in the amino acid sequence of AAV2 VP1 capsid protein, and said position is based on the amino acid sequence of wild-type AAV2 VP1 capsid protein shown by SEQ ID NO: 2, and
   wherein the mutant is a mutant of AAV2 capsid protein.

2. The mutant of an AAV capsid protein according to claim 1, wherein the one or more amino acid replacements comprise a replacement of alanine at position 68 by valine (A68V), in the amino acid sequence of AAV2 VP1 capsid protein, and said position is based on the amino acid sequence of wild-type AAV2 VP1 capsid protein shown by SEQ ID NO: 2.

3. The mutant of an AAV capsid protein according to claim 1, wherein the one or more amino acid replacements comprise:
   (a) a replacement of alanine at position 3 by threonine (A3T),
   (b) a replacement of tyrosine at position 6 by histidine (Y6H), and
   (c) a replacement of alanine at position 68 by valine (A68V)
   in the amino acid sequence of AAV2 VP1 capsid protein, and the positions indicated in (a) to (c) are based on the amino acid sequence of wild-type AAV2 VP1 capsid protein shown by SEQ ID NO: 2.

4. A recombinant AAV particle containing the mutant of an AAV capsid protein according to claim 1.

5. A composition containing the recombinant AAV particle according to claim 4.

6. A method of introducing a gene into a target cell, the method comprising a step of bringing the recombinant AAV particle according to claim 4 into contact with a target cell.

* * * * *

SEQUENCE LISTING

<160> NUMBER OF SEQ ID NOS: 18

<210> SEQ ID NO 1
<211> LENGTH: 2208
<212> TYPE: DNA
<213> ORGANISM: adeno-associated virus 2

<400> SEQUENCE: 1

```
atggctgccg atggttatct tccagattgg ctcgaggaca ctctctctga aggaataaga      60
cagtggtgga agctcaaacc tggcccacca ccaccaaagc ccgcagagcg gcataaggac     120
gacagcaggg gtcttgtgct tcctgggtac aagtacctcg gacccttcaa cggactcgac     180
```

-continued

```
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa dacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact     600 aatacgatgg ctacaggcag tggcgcacca atggcagaca taacgagggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg gctacagcac cccttggggg    840
tattttgact tcaacagatt ccactgccac gtgactggca agactcatc                900 aacaacaact ggggattccg acccaagaga ctcaacttca gctctttaa cattcaagtc    960 aaagaggtca cgcagaatga cggtacgacg acgattgcca ataaccttac cagcacggtt    1020
caggtgttta ctgactcgga gtaccagctc ccgtacgtcc tcggctcggc gcatcaagga    1080
tgcctcccgc cgttcccagc agacgtcttc atggtgccac agtatggata cctcaccctg    1140
aacaacggga gtcaggcagt aggacgctct tcattttact gcctggagta ctttcccttct    1200 cagatgctgc gtaccggaaa caactttacc ttcagctaca cttttgagga cgttcctttc    1260
cacagcagct acgctcacag ccagagtctg accgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctccctca tgggtggatt cggacttaaa    1920
caccctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatccaga aattcagtac    2100
acttccaact acaacaagtc tgttaatgtg gactttactg tggacactaa tggcgtgtat    2160
tcagagcctc gccccattgg caccagatac ctgactcgta atctgtaa                 2208
```

<210> SEQ ID NO 2
<211> LENGTH: 735
<212> TYPE: PRT
<213> ORGANISM: adeno-associated virus 2

<400> SEQUENCE: 2

```
Met Ala Ala Asp Gly Tyr Leu Pro Asp Trp Leu Glu Asp Thr Leu Ser
1               5                   10                  15
```

-continued

```
Glu Gly Ile Arg Gln Trp Trp Lys Leu Lys Pro Gly Pro Pro Pro
             20                  25                  30
Lys Pro Ala Glu Arg His Lys Asp Asp Ser Arg Gly Leu Val Leu Pro
         35                  40                  45
Gly Tyr Lys Tyr Leu Gly Pro Phe Asn Gly Leu Asp Lys Gly Glu Pro
     50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
```

-continued

```
            435                 440                 445
Asn Thr Pro Ser Gly Thr Thr Thr Gln Ser Arg Leu Gln Phe Ser Gln
    450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
            500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735
```

<210> SEQ ID NO 3
<211> LENGTH: 2208
<212> TYPE: DNA
<213> ORGANISM: Artificial Sequence
<220> FEATURE:
<223> OTHER INFORMATION: nucleic acid sequence coding AAV2 VP1(A68V)

<400> SEQUENCE: 3

```
atggctgccg atggttatct tccagattgg ctcgaggaca ctctctctga aggaataaga     60
cagtggtgga agctcaaacc tggcccacca ccaccaaagc ccgcagagcg cataaggac    120
gacagcaggg gtcttgtgct tcctgggtac aagtacctcg acccttcaa cggactcgac    180
aagggagagc cggtcaacga ggtagacgcc gcggccctcg agcacgacaa agcctacgac    240
cggcagctcg acagcggaga caaccccgta ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa dacggctccg    420
```

-continued

```
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg accccagcc tctcggacag ccaccagcag cccctctgg tctgggaact    600 aatacgatgg ctacaggcag tggcgcacca atggcagaca taacgaggg cgccgacgga    660 gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg ctacagcac cccttggggg    840 tattttgact tcaacagatt ccactgccac ttttcaccac gtgactggca agactcatc    900 aacaacaact ggggattccg acccaagaga ctcaacttca gctctttaa cattcaagtc    960 aaagaggtca cgcagaatga cggtacgacg acgattgcca ataaccttac cagcacggtt   1020
caggtgttta ctgactcgga gtaccagctc ccgtacgtcc tcggctcggc catcaagga   1080 tgcctcccgc cgttcccagc agacgtcttc atggtgccac agtatggata cctcaccctg   1140
aacaacggga gtcaggcagt aggacgctct tcatttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt tcctcagag cggggttctc   1620 atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctgtaa              2208
```

<210> SEQ ID NO 4
<211> LENGTH: 735
<212> TYPE: PRT
<213> ORGANISM: Artificial Sequence
<220> FEATURE:
<223> OTHER INFORMATION: amino acid sequence of AAV2 VP1(A68V)

<400> SEQUENCE: 4

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45
```

```
Gly Tyr Lys Tyr Leu Gly Pro Phe Asn Gly Leu Asp Lys Gly Glu Pro
 50                  55                  60

Val Asn Glu Val Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460
```

```
Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 5
<211> LENGTH: 2208
<212> TYPE: DNA
<213> ORGANISM: Artificial Sequence
<220> FEATURE:
<223> OTHER INFORMATION: nucleic acid sequence coding AAV2
      VP1(A3T/Y6H/A68V)

<400> SEQUENCE: 5

```
atggctaccg atggtcatct tccagattgg ctcgaggaca ctctctctga aggaataaga      60
cagtggtgga agctcaaacc tggcccacca ccaccaaagc cgcagagcg gcataaggac      120 gacagcaggg gtcttgtgct tcctgggtac aagtacctcg acccttcaa cggactcgac      180 aagggagagc cggtcaacga ggtagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt ggggcaacc tcggacgagc agtcttccag      360
gcgaaaaaga gggttcttga acctctgggc ctggttgagg aacctgttaa dacggctccg      420 ggaaaaaga ggccggtaga gcactctcct gtggagccag actcctcctc gggaaccgga      480
aaggcgggcc agcagcctgc aagaaaaaga ttgaattttg gtcagactgg agacgcagac      540
```

```
tcagtacctg accccagcc tctcggacag ccaccagcag cccctctgg tctgggaact    600 aatacgatgg ctacaggcag tggcgcacca atggcagaca taacgaggg cgccgacgga    660 gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg ctacagcac cccttggggg    840 tattttgact tcaacagatt ccactgccac ttttcaccac gtgactggca agactcatc     900 aacaacaact ggggattccg acccaagaga ctcaacttca gctcttttaa cattcaagtc    960
aaagaggtca cgcagaatga cggtacgacg acgattgcca ataaccttac cagcaccgtt    1020 caggtgtttta ctgactcgga gtaccagctc ccgtacgtcc tcggctcggc catcaagga   1080 tgcctcccgc cgttccagc agacgtcttc atggtgccac agtatggata cctcaccctg    1140
aacaacggga gtcaggcagt aggacgctct tcatttact gcctggagta ctttccttct    1200
cagatgctgc gtaccggaaa caactttacc ttcagctaca cttttgagga cgttcctttc   1260
cacagcagct acgctcacag ccagagtctg accgtctca tgaatcctct catcgaccag    1320
tacctgtatt acttgagcag aacaaacact ccaagtggaa ccaccacgca gtcaaggctt    1380
cagttttctc aggccggagc gagtgacatt cgggaccagt ctaggaactg gcttcctgga    1440
ccctgttacc gccagcagcg agtatcaaag acatctgcgg ataacaacaa cagtgaatac    1500
tcgtggactg gagctaccaa gtaccacctc aatggcagag actctctggt gaatccgggc    1560
ccggccatgg caagccacaa ggacgatgaa gaaaagtttt tccctcagag cggggttctc    1620
atctttggga agcaaggctc agagaaaaca aatgtggaca ttgaaaaggt catgattaca    1680
gacgaagagg aaatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtctggca ggacagagat gtgtaccttc aggggcccat ctgggcaaag    1860
attccacaca cggacggaca ttttcacccc tctccctca tgggtggatt cggacttaaa    1920 cacctcctc cacagattct catcaagaac accccggtac ctgcgaatcc ttcgaccacc    1980
ttcagtgcgg caaagtttgc ttccttcatc acacagtact ccacgggaca ggtcagcgtg    2040
gagatcgagt gggagctgca gaaggaaaac agcaaacgct ggaatccga aattcagtac    2100 acttccaact acaacaagtc tgttaatgtg gactttactg tggacactaa tggcgtgtat    2160
tcagagcctc gccccattgg caccagatac ctgactcgta atctgtaa                2208
```

<210> SEQ ID NO 6
<211> LENGTH: 735
<212> TYPE: PRT
<213> ORGANISM: Artificial Sequence
<220> FEATURE:
<223> OTHER INFORMATION: amino acid sequence of AAV2 VP1(A3T/Y6H/A68V)

<400> SEQUENCE: 6

```
Met Ala Thr Asp Gly His Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Glu Val Asp Ala Ala Leu Glu His Asp Lys Ala Tyr Asp
 65                  70                  75                  80

Arg Gln Leu Asp Ser Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
```

485                 490                 495
Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 7
<211> LENGTH: 8177
<212> TYPE: DNA
<213> ORGANISM: Artificial Sequence
<220> FEATURE:
<223> OTHER INFORMATION: pAAV-Ad-ACG2

<400> SEQUENCE: 7
aattcccatc atcaataata taccttattt tggattgaag ccaatatgat aatgaggggg      60
tggagtttgt gacgtggcgc ggggcgtggg aacggggcgg gtgacgtagt agtctctaga     120
ggtcctgtat tagaggtcac gtgagtgttt tgcgacattt tgcgacacca tgtggtcacg     180
ctgggtattt aagcccgagt gagcacgcag ggtctccatt ttgaagcggg aggtttgaac     240
gcgcagccac cacgccgggg ttttacgaga ttgtgattaa ggtccccagc gaccttgacg     300
ggcatctgcc cggcatttct gacagctttg tgaactgggt ggccgagaag gaatgggagt     360
tgccgccaga ttctgacatg gatctgaatc tgattgagca ggcacccctg accgtggccg     420
agaagctgca gcgcgacttt ctgacggaat ggcgccgtgt gagtaaggcc ccggaggccc     480
ttttctttgt gcaatttgag aagggagaga gctacttcca catgcacgtg ctcgtggaaa     540
ccaccggggt gaaatccatg gtttgggac gtttcctgag tcagattcgc gaaaaactga     600
ttcagagaat ttaccgcggg atcgagccga ctttgccaaa ctggttcgcg gtcacaaaga     660

```
ccagaaatgg cgccggaggc gggaacaagg tggtggatga gtgctacatc cccaattact    720
tgctccccaa aacccagcct gagctccagt gggcgtggac taatatggaa cagtatttaa    780
gcgcctgttt gaatctcacg gagcgtaaac ggttggtggc gcagcatctg acgcacgtgt    840
cgcagacgca ggagcagaac aaagagaatc agaatcccaa ttctgatgcg ccggtgatca    900
gatcaaaaac ttcagccagg tacatggagc tggtcgggtg gctcgtggac aaggggatta    960
cctcggagaa gcagtggatc caggaggacc aggcctcata catctccttc aatgcggcct   1020
ccaactcgcg gtcccaaatc aaggctgcct tggacaatgc gggaaagatt atgagcctga   1080
ctaaaaccgc ccccgactac ctggtggggcc agcagcccgt ggaggacatt ccagcaatc   1140
ggatttataa aattttggaa ctaaacgggt acgatcccca atatgcggct ccgtctttc   1200
tgggatgggc cacgaaaaag ttcggcaaga ggaacaccat ctggctgttt ggcctgcaa   1260
ctaccgggaa gaccaacatc gcggaggcca tagcccacac tgtgcccttc tacgggtgcg   1320
taaactggac caatgagaac tttcccttca acgactgtgt cgacaagatg gtgatctggt   1380
gggaggaggg gaagatgacc gccaaggtcg tggagtcggc caaagccatt ctcggaggaa   1440
gcaaggtgcg cgtggaccag aaatgcaagt cctcggccca gatagacccg actcccgtga   1500
tcgtcacctc caacaccaac atgtgcgccg tgattgacgg gaactcaacg accttcgaac   1560
accagcagcc gttgcaagac cggatgttca aatttgaact caccccgccgt ctggatcatg   1620
actttgggaa ggtcaccaag caggaagtca agacttttt ccggtgggca aaggatcacg   1680
tggttgaggt ggagcatgaa ttctacgtca aaaagggtgg agccaagaaa agacccgccc   1740
ccagtgacgc agatataagt gagcccaaac gggtgcgcga gtcagttgcg cagccatcga   1800
cgtcagacgc ggaagcttcg atcaactacg cagacaggta ccaaaacaaa tgttctcgtc   1860
acgtgggcat gaatctgatg ctgtttccct gcagacaatg cgagagaatg aatcagaatt   1920
caaatatctg cttcactcac ggacagaaag actgtttaga gtgctttccc gtgtcagaat   1980
ctcaacccgt ttctgtcgtc aaaaaggcgt atcagaaact gtgctacatt catcatatca   2040
tgggaaaggt gccagacgct tgcactgcct gcgatctggt caatgtggat ttggatgact   2100
gcatctttga acaataaatg atttaaatca ggtatggctg ccgatggtta tcttccagat   2160
tggctcgagg acactctctc tgaaggaata agacagtggt ggaagctcaa acctggccca   2220
ccaccaccaa agcccgcaga gcggcataag gacgacagca ggggtcttgt tcttcctggg   2280
tacaagtacc tcggacccctt caacggactc gacaagggag agccggtcaa cgaggcagac   2340
gccgcggccc tcgagcacga caaagcctac gaccggcagc tcgacagcgg agacaacccg   2400
tacctcaagt acaaccacgc cgacgcggag tttcaggagc gccttaaaga agatacgtct   2460
tttgggggca acctcggacg agcagtcttc caggcgaaaa agagggttct tgaacctctg   2520
ggcctggttg aggaacctgt taagacggct ccgggaaaaa agaggccggt agagcactct   2580
cctgtggagc cagactcctc ctcgggaacc ggaaaggcgg ccagcagcc tgcaagaaaa   2640
agattgaatt ttggtcagac tggagacgca gactcagtac ctgaccccca gcctctcgga   2700
cagccaccag cagcccctc tggtctggga actaatacga tggcaacagg cagtggcgca   2760
ccaatggcag acaataacga gggcgccgac ggggtgggta attcctcggg aaattggcat   2820
tgcgattcca catggatggg cgacagagtc atcaccacca gcaccgaac ctgggccctg   2880
cccacctaca caaccaccct ctacaaacaa atttccagcc aatcaggagc tcgaacgac   2940
aatcactact ttggctacag caccccttgg gggtattttg acttcaacag attccactgc   3000
cactttttcac cacgtgactg gcaaagactc atcaacaaca actgggggatt ccgacccaag   3060
```

-continued

```
agactcaact tcaagctctt taacattcaa gtcaaagagg tcacgcagaa tgacggtacg    3120
acgacgattg ccaataacct taccagcacg gttcaggtgt ttactgactc ggagtaccag    3180
ctcccgtacg tcctcggctc ggcgcatcaa ggatgcctcc cgccgttccc agcagacgtc    3240
ttcatggtgc cacagtatgg atacctcacc ctgaacaacg ggagtcaggc agtaggacgc    3300
tcttcatttt actgcctgga gtactttcct tctcagatgc tgcgtaccgg aaacaacttt    3360
accttcagct acacttttga ggacgttcct ttccacagca gctacgctca cagccagagt    3420
ctggaccgtc tcatgaatcc tctcatcgac cagtacctgt attacttgag cagaacaaac    3480
actccaagtg gaaccaccac gcagtcaagg cttcagtttt tcaggccgg agcgagtgac     3540 attcgggacc agtctaggaa ctggcttcct ggaccctgtt accgccagca gcgagtatca    3600
aagacatctg cggataacaa caacagtgaa tactcgtgga ctggagctac caagtaccac    3660
ctcaatggca gagactctct ggtgaatccg ggcccggcca tggcaagcca caggacgat     3720 gaagaaaagt ttttttcctca gagcggggtt ctcatctttg ggaagcaagg ctcagagaaa    3780
gcaaatgtgg acattgaaaa ggtcatgatt acagacgaag aggaaatcag gacaaccaat    3840
cccgtggcta cggagcagta tggttctgta tctaccaacc tccagagagg caacagacaa    3900
gcagctaccg cagatgtcaa cacacaaggc gttcttccag gcatggtctg gcaggacaga    3960
gatgtgtacc ttcaggggcc catctgggca aagattccac acacggacgg acattttcac    4020
ccctctcccc tcatgggtgg attcggactt aaacaccctc ctccacagat tctcatcaag    4080
aacaccccgg tacctgcgaa tccttcgacc accttcagtg cggcaaagtt tgcttccttc    4140
atcacacagt actccacggg acaggtcagc gtggagatcg agtgggagct gcagaaggaa    4200
aacagcaaac gctggaatcc cgaaattcag tacacttcca actacaacaa gtctgttaat    4260
gtggacttta ctgtggacac taatggcgtg tattcagagc ctcgcccat ggcaccaga      4320 tacctgactc gtaatctgta attgcttgtt aatcaataaa ccgtttaatt cgtttcagtt    4380
gaactttggt ctctgcgtat ttcttttctta tctagttttcc atgctctaga ctactacgtc    4440
acccgccccg ttcccacgcc ccgcgccacg tcacaaactc caccccctca ttatcatatt    4500
ggcttcaatc caaaataagg tatattattg atgatgcatc gctggcgtaa tagcgaagag    4560
gcccgcaccg atcgcccttc ccaacagttg cgcagcctga atggcgaatg gaattccaga    4620
cgattgagcg tcaaaatgta ggtatttcca tgagcgtttt tcctgttgca atggctggcg    4680
gtaatattgt tctggatatt accagcaagg ccgatagttt gagttcttct actcaggcaa    4740
gtgatgttat tactaatcaa agaagtattg cgacaacggt taatttgcgt gatggacaga    4800
ctcttttact cggtggcctc actgattata aaaacacttc tcaggattct ggcgtaccgt    4860
tcctgtctaa aatccctta atcggcctcc tgtttagctc ccgctctgat tctaacgagg    4920
aaagcacgtt atacgtgctc gtcaaagcaa ccatagtacg cgccctgtag cggcgcatta    4980
agcgcggcgg gtgtggtggt tacgcgcagc gtgaccgcta cacttgccag cgccctagcg    5040
cccgctcctt tcgctttctt cccttccttt ctcgccacgt tcgccggctt tccccgtcaa    5100
gctctaaatc gggggctccc tttagggttc cgatttagtg ctttacggca cctcgacccc    5160
aaaaaacttg attagggtga tggttcacgt agtgggccat cgccctgata gacggttttt    5220
cgccctttga cgttggagtc cacgttcttt aatagtggac tcttgttcca aactggaaca    5280
acactcaacc ctatctcggt ctattctttt gatttataag ggattttgcc gatttcggcc    5340
tattggttaa aaaatgagct gatttaacaa aaatttaacg cgaattttaa caaaatatta    5400
```

-continued

| | | | | | |
|---|---|---|---|---|---|
| acgtttacaa | tttaaatatt | tgcttataca | atcttcctgt | ttttggggct | tttctgatta | 5460 |
| tcaaccgggg | tacatatgat | tgacatgcta | gttttacgat | taccgttcat | cgattctctt | 5520 |
| gtttgctcca | gactctcagg | caatgacctg | atagcctttg | tagagacctc | tcaaaaatag | 5580 |
| ctaccctctc | cggcatgaat | ttatcagcta | gaacggttga | atatcatatt | gatggtgatt | 5640 |
| tgactgtctc | cggcctttct | cacccgtttg | aatctttacc | tacacattac | tcaggcattg | 5700 |
| catttaaaat | atatgagggt | tctaaaaatt | tttatccttg | cgttgaaata | aaggcttctc | 5760 |
| ccgcaaaagt | attacagggt | cataatgttt | ttggtacaac | cgatttagct | ttatgctctg | 5820 |
| aggctttatt | gcttaatttt | gctaattctt | tgccttgcct | gtatgattta | ttggatgttg | 5880 |
| gaattcctga | tgcggtattt | tctccttacg | catctgtgcg | gtatttcaca | ccgcatatgg | 5940 |
| tgcactctca | gtacaatctg | ctctgatgcc | gcatagttaa | gccagccccg | acacccgcca | 6000 |
| acacccgctg | acgcgccctg | acgggcttgt | ctgctcccgg | catccgctta | cagacaagct | 6060 |
| gtgaccgtct | ccgggagctg | catgtgtcag | aggttttcac | cgtcatcacc | gaaacgcgcg | 6120 |
| agacgaaagg | gcctcgtgat | acgcctattt | ttataggtta | atgtcatgat | aataatggtt | 6180 |
| tcttagacgt | caggtggcac | ttttcgggga | aatgtgcgcg | gaaccccctat | ttgtttattt | 6240 |
| ttctaaatac | attcaaatat | gtatccgctc | atgagacaat | aaccctgata | aatgcttcaa | 6300 |
| taatattgaa | aaaggaagag | tatgagtatt | caacatttcc | gtgtcgccct | tattcccttt | 6360 |
| tttgcggcat | tttgccttcc | tgtttttgct | cacccagaaa | cgctggtgaa | agtaaaagat | 6420 |
| gctgaagatc | agttgggtgc | acgagtgggt | tacatcgaac | tggatctcaa | cagcggtaag | 6480 |
| atccttgaga | gttttcgccc | cgaagaacgt | tttccaatga | tgagcacttt | taaagttctg | 6540 |
| ctatgtggcg | cggtattatc | ccgtattgac | gccgggcaag | agcaactcgg | tcgccgcata | 6600 |
| cactattctc | agaatgactt | ggttgagtac | tcaccagtca | cagaaaagca | tcttacggat | 6660 |
| ggcatgacag | taagagaatt | atgcagtgct | gccataacca | tgagtgataa | cactgcggcc | 6720 |
| aacttacttc | tgacaacgat | cggaggaccg | aaggagctaa | ccgcttttt | gcacaacatg | 6780 |
| ggggatcatg | taactcgcct | tgatcgttgg | gaaccggagc | tgaatgaagc | cataccaaac | 6840 |
| gacgagcgtg | acaccacgat | gcctgtagca | atggcaacaa | cgttgcgcaa | actattaact | 6900 |
| ggcgaactac | ttactctagc | ttcccggcaa | caattaatag | actggatgga | ggcggataaa | 6960 |
| gttgcaggac | cacttctgcg | ctcggccctt | ccggctggct | ggtttattgc | tgataaatct | 7020 |
| ggagccggtg | agcgtgggtc | tcgcggtatc | attgcagcac | tggggccaga | tggtaagccc | 7080 |
| tcccgtatcg | tagttatcta | cacgacgggg | agtcaggcaa | ctatggatga | acgaaataga | 7140 |
| cagatcgctg | agataggtgc | ctcactgatt | aagcattggt | aactgtcaga | ccaagtttac | 7200 |
| tcatatatac | tttagattga | tttaaaactt | cattttaat | ttaaaggat | ctaggtgaag | 7260 |
| atcctttttg | ataatctcat | gaccaaaatc | ccttaacgtg | agttttcgtt | ccactgagcg | 7320 |
| tcagacccccg | tagaaaagat | caaaggatct | tcttgagatc | cttttttct | gcgcgtaatc | 7380 |
| tgctgcttgc | aaacaaaaaa | accaccgcta | ccagcggtgg | tttgtttgcc | ggatcaagag | 7440 |
| ctaccaactc | tttttccgaa | ggtaactggc | ttcagcagag | cgcagatacc | aaatactgtc | 7500 |
| cttctagtgt | agccgtagtt | aggccaccac | ttcaagaact | ctgtagcacc | gcctacatac | 7560 |
| ctcgctctgc | taatcctgtt | accagtggct | gctgccagtg | gcgataagtc | gtgtcttacc | 7620 |
| gggttggact | caagacgata | gttaccggat | aaggcgcagc | ggtcgggctg | aacggggggt | 7680 |
| tcgtgcacac | agcccagctt | ggagcgaacg | acctacaccg | aactgagata | cctacagcgt | 7740 |
| gagctatgag | aaagcgccac | gcttcccgaa | gggagaaagg | cggacaggta | tccggtaagc | 7800 |

```
ggcagggtcg gaacaggaga gcgcacgagg gagcttccag ggggaaacgc ctggtatctt    7860
tatagtcctg tcgggtttcg ccacctctga cttgagcgtc gattttttgtg atgctcgtca   7920 ggggggcgga gcctatggaa aaacgccagc aacgcggcct ttttacggtt cctggccttt    7980
tgctggcctt ttgctcacat gttctttcct gcgttatccc ctgattctgt ggataaccgt    8040
attaccgcct ttgagtgagc tgataccgct cgccgcagcc gaacgaccga gcgcagcgag    8100
tcagtgagcg aggaagcgga agagcgccca atacgcaaac cgcctctccc cgcgcgttgg    8160
ccgattcatt aatgcag                                                   8177
```

<210> SEQ ID NO 8
<211> LENGTH: 33
<212> TYPE: DNA
<213> ORGANISM: Artificial Sequence
<220> FEATURE:
<223> OTHER INFORMATION: mutant-1F primer

<400> SEQUENCE: 8
atcaggtatg gctaccgatg gtcatcttcc aga                                 33

<210> SEQ ID NO 9
<211> LENGTH: 33
<212> TYPE: DNA
<213> ORGANISM: Artificial Sequence
<220> FEATURE:
<223> OTHER INFORMATION: mutant-1R primer

<400> SEQUENCE: 9
tctggaagat gaccatcggt agccatacct gat                                 33

<210> SEQ ID NO 10
<211> LENGTH: 33
<212> TYPE: DNA
<213> ORGANISM: Artificial Sequence
<220> FEATURE:
<223> OTHER INFORMATION: mutant-2F primer

<400> SEQUENCE: 10
agccggtcaa cgaggtagac gccgcggccc tcg                                 33

<210> SEQ ID NO 11
<211> LENGTH: 33
<212> TYPE: DNA
<213> ORGANISM: Artificial Sequence
<220> FEATURE:
<223> OTHER INFORMATION: mutant-2R primer

<400> SEQUENCE: 11
cgagggccgc ggcgtctacc tcgttgaccg gct                                 33

<210> SEQ ID NO 12
<211> LENGTH: 5770
<212> TYPE: DNA
<213> ORGANISM: Artificial Sequence
<220> FEATURE:
<223> OTHER INFORMATION: pAAV-CB-EGFP

<400> SEQUENCE: 12

```
cagcagctgg cgtaatagcg aagaggcccg caccgatcgc ccttcccaac agttgcgcag     60
cctgaatggc gaatggaatt ccagacgatt gagcgtcaaa atgtaggtat ttccatgagc    120 gttttttcctg ttgcaatggc tggcggtaat attgttctgg atattaccag caaggccgat   180
```

```
agtttgagtt cttctactca ggcaagtgat gttattacta atcaaagaag tattgcgaca      240
acggttaatt tgcgtgatgg acagactctt ttactcggtg gcctcactga ttataaaaac      300
acttctcagg attctggcgt accgttcctg tctaaaatcc ctttaatcgg cctcctgttt      360
agctcccgct ctgattctaa cgaggaaagc acgttatacg tgctcgtcaa agcaaccata      420
gtacgcgccc tgtagcggcg cattaagcgc ggcgggtgtg gtggttacgc gcagcgtgac      480
cgctacactt gccagcgccc tagcgcccgc tcctttcgct ttcttccctt cctttctcgc      540
cacgttcgcc ggctttcccc gtcaagctct aaatcggggg ctccctttag ggttccgatt      600
tagtgcttta cggcacctcg accccaaaaa acttgattag ggtgatggtt cacgtagtgg      660
gccatcgccc tgatagacgg ttttcgccc tttgacgttg gagtccacgt tctttaatag      720
tggactcttg ttccaaactg gaacaacact caacccatc tcggtctatt cttttgattt      780
ataagggatt ttgccgattt cggcctattg gttaaaaaat gagctgattt aacaaaaatt      840
taacgcgaat tttaacaaaa tattaacgtt tacaatttaa atatttgctt atacaatctt      900
cctgtttttg ggcttttct gattatcaac cggggtacat atgattgaca tgctagtttt      960
acgattaccg ttcatcgcct gcactgcgcg ctcgctcgct cactgaggcc gcccgggcaa     1020
agcccgggcg tcgggcgacc tttggtcgcc cggcctcagt gagcgagcga gcgcgcagag     1080
agggagtgga attcacgcgt ggtacgatct gaattcggta caattcacgc gtggtacctc     1140
tggtcgttac ataacttacg gtaaatggcc cgcctggctg accgcccaac gacccgccc     1200 attgacgtca ataatgacgt atgttcccat agtaacgcca atagggactt tccattgacg     1260
tcaatgggtg gagtatttac ggtaaactgc ccacttggca gtacatcaag tgtatcatat     1320
gccaagtacg cccctattg acgtcaatga cggtaaatgg cccgcctggc attatgccca     1380
gtacatgacc ttatgggact ttcctacttg gcagtacatc tactcgaggc cacgttctgc     1440
ttcactctcc ccatctcccc cccctcccca ccccaatttt gtatttatt tatttttaa     1500 ttattttgtg cagcgatggg ggcgggggggg gggggggggg gggcgcgcgc caggcggggc     1560 ggggcgggc gaggggcggg gcggggcgag gcggagaggt gcggcggcag ccaatcagag     1620
cggcgcgctc cgaaagtttc cttttatggc gaggcggcgg cggcggcggc cctataaaa     1680 gcgaagcgcg cggcgggcgg gagcgggatc agccaccgcg gtggcggccc tagagtcgat     1740
cgaggaactg aaaaaccaga aagttaactg gtaagtttag tcttttttgtc ttttatttca     1800 ggtcccggat ccggtggtgg tgcaaatcaa agaactgctc ctcagtggat gttgccttta     1860
cttctaggcc tgtacggaag tgttacttct gctctaaaag ctgcggaatt gtacccgcgg     1920
ccgatccacc ggtcgccacc atggtgagca agggcgagga gctgttcacc ggggtggtgc     1980
ccatcctggt cgagctggac ggcgacgtaa acggccacaa gttcagcgtg tccggcgagg     2040
gcgagggcga tgccacctac ggcaagctga ccctgaagtt catctgcacc accggcaagc     2100
tgcccgtgcc ctggcccacc ctcgtgacca cctgacccta cggcgtgcag tgcttcagcc     2160
gctaccccga ccacatgaag cagcacgact tcttcaagtc cgccatgccc gaaggctacg     2220
tccaggagcg caccatcttc ttcaaggacg acggcaacta caagacccgc gccgaggtga     2280
agttcgaggg cgacaccctg gtgaaccgca tcgagctgaa gggcatcgac ttcaaggagg     2340
acggcaacat cctggggcac aagctggagt acaactacaa cagccacaac gtctatatca     2400
tggccgacaa gcagaagaac ggcatcaagg tgaacttcaa gatccgccac aacatcgagg     2460
acggcagcgt gcagctcgcc gaccactacc agcagaacac ccccatcggc gacggccccg     2520
tgctgctgcc cgacaaccac tacctgagca cccagtccgc cctgagcaaa gaccccaacg     2580
```

```
agaagcgcga tcacatggtc ctgctggagt tcgtgaccgc cgccgggatc actctcggca   2640
tggacgagct gtacaagtaa agcggccatc aagcttatcg ataccgtcga ctagagctcg   2700
ctgatcagcc tcgactgtgc cttctagttg ccagccatct gttgtttgcc cctcccccgt   2760
gccttccttg accctggaag gtgccactcc cactgtcctt tcctaataaa atgaggaaat   2820
tgcatcgcat tgtctgagta ggtgtcattc tattctgggg gtgggtgg ggcaggacag     2880 caaggggag gattgggaag acaatagcag gcatgctggg gagagatcga tctaggaacc    2940
cctagtgatg gagttggcca ctccctctct gcgcgctcgc tcgctcactg aggccgcccg   3000
ggcaaagccc gggcgtcggg cgacctttgg tcgcccggcc tcagtgagcg agcgagcgcg   3060
cagagaggga gtggccaacc ccccccccc ccccctgca tgcaggcgat tctcttgttt     3120
gctccagact ctcaggcaat gacctgatag cctttgtaga gacctctcaa aaatagctac   3180
cctctccggc atgaatttat cagctagaac ggttgaatat catattgatg gtgatttgac   3240
tgtctccggc ctttctcacc cgtttgaatc tttacctaca cattactcag gcattgcatt   3300
taaaatatat gagggttcta aaaattttta tccttgcgtt gaaataaagg cttctcccgc   3360
aaaagtatta cagggtcata atgttttttgg tacaaccgat ttagctttat gctctgaggc   3420
tttattgctt aattttgcta attctttgcc ttgcctgtat gatttattgg atgttggaat   3480
tcctgatgcg gtattttctc cttacgcatc tgtgcggtat ttcacaccgc atatggtgca   3540
ctctcagtac aatctgctct gatgccgcat agttaagcca gccccgacac ccgccaacac   3600
ccgctgacgc gccctgacgg gcttgtctgc tcccggcatc cgcttacaga caagctgtga   3660
ccgtctccgg gagctgcatg tgtcagaggt tttcaccgtc atcaccgaaa cgcgcgagac   3720
gaaagggcct cgtgatacgc ctatttttat aggttaatgt catgataata atggtttctt   3780
agacgtcagg tggcactttt cggggaaatg tgcgcggaac ccctatttgt ttatttttct   3840
aaatacattc aaatatgtat ccgctcatga gacaataacc ctgataaatg cttcaataat   3900
attgaaaaag gaagagtatg agtattcaac atttccgtgt cgcccttatt cccttttttg   3960
cggcattttg ccttcctgtt tttgctcacc cagaaacgct ggtgaaagta aaagatgctg   4020
aagatcagtt gggtgcacga gtgggttaca tcgaactgga tctcaacagc ggtaagatcc   4080
ttgagagttt tcgccccgaa gaacgttttc caatgatgag cacttttaaa gttctgctat   4140
gtggcgcggt attatcccgt attgacgccg ggcaagagca actcggtcgc cgcatacact   4200
attctcagaa tgacttggtt gagtactcac cagtcacaga aaagcatctt acggatggca   4260
tgacagtaag agaattatgc agtgctgcca taaccatgag tgataacact gcggccaact   4320
tacttctgac aacgatcgga ggaccgaagg agctaaccgc ttttttgcac aacatggggg   4380
atcatgtaac tcgccttgat cgttgggaac cggagctgaa tgaagccata ccaaacgacg   4440
agcgtgacac cacgatgcct gtagcaatgg caacaacgtt gcgcaaacta ttaactggcg   4500
aactacttac tctagcttcc cggcaacaat taatagactg gatggaggcg gataaagttg   4560
caggaccact tctgcgctcg gcccttccgg ctggctggtt tattgctgat aaatctggag   4620
ccggtgagcg tgggtctcgc ggtatcattg cagcactggg gccagatggt aagccctccc   4680
gtatcgtagt tatctacacg acggggagtc aggcaactat ggatgaacga aatagacaga   4740
tcgctgagat aggtgcctca ctgattaagc attggtaact gtcagaccaa gtttactcat   4800
atatacttta gattgattta aaacttcatt tttaatttaa aaggatctag gtgaagatcc   4860 ttttttgataa tctcatgacc aaaatccctt aacgtgagtt ttcgttccac tgagcgtcag   4920
```

| | |
|---|---|
| acccgtaga aaagatcaaa ggatcttctt gagatccttt ttttctgcgc gtaatctgct | 4980 |
| gcttgcaaac aaaaaaacca ccgctaccag cggtggtttg tttgccggat caagagctac | 5040 |
| caactctttt tccgaaggta actggcttca gcagagcgca gataccaaat actgtccttc | 5100 |
| tagtgtagcc gtagttaggc caccacttca agaactctgt agcaccgcct acatacctcg | 5160 |
| ctctgctaat cctgttacca gtggctgctg ccagtggcga taagtcgtgt cttaccgggt | 5220 |
| tggactcaag acgatagtta ccggataagg cgcagcggtc gggctgaacg ggggttcgt | 5280 |
| gcacacagcc cagcttggag cgaacgacct acaccgaact gagataccta cagcgtgagc | 5340 |
| tatgagaaag cgccacgctt cccgaaggga gaaaggcgga caggtatccg gtaagcggca | 5400 |
| gggtcggaac aggagagcgc acgagggagc ttccaggggg aaacgcctgg tatctttata | 5460 |
| gtcctgtcgg gtttcgccac ctctgacttg agcgtcgatt tttgtgatgc tcgtcagggg | 5520 |
| ggcggagcct atggaaaaac gccagcaacg cggccttttt acggttcctg gccttttgct | 5580 |
| ggccttttgc tcacatgttc tttcctgcgt tatcccctga ttctgtggat aaccgtatta | 5640 |
| ccgcctttga gtgagctgat accgctcgcc gcagccgaac gaccgagcgc agcgagtcag | 5700 |
| tgagcgagga agcggaagag cgcccaatac gcaaaccgcc tctccccgcg cgttggccga | 5760 |
| ttcattaatg | 5770 |

```
<210> SEQ ID NO 13
<211> LENGTH: 21
<212> TYPE: DNA
<213> ORGANISM: Artificial Sequence
<220> FEATURE:
<223> OTHER INFORMATION: ITR-F primer

<400> SEQUENCE: 13
```

| | |
|---|---|
| ggaacccta gtgatggagt t | 21 |

```
<210> SEQ ID NO 14
<211> LENGTH: 16
<212> TYPE: DNA
<213> ORGANISM: Artificial Sequence
<220> FEATURE:
<223> OTHER INFORMATION: ITR-R primer

<400> SEQUENCE: 14
```

| | |
|---|---|
| cggcctcagt gagcga | 16 |

```
<210> SEQ ID NO 15
<211> LENGTH: 19
<212> TYPE: DNA
<213> ORGANISM: Artificial Sequence
<220> FEATURE:
<223> OTHER INFORMATION: hamster-actin-F primer

<400> SEQUENCE: 15
```

| | |
|---|---|
| gtggccatct cttgcttga | 19 |

```
<210> SEQ ID NO 16
<211> LENGTH: 21
<212> TYPE: DNA
<213> ORGANISM: Artificial Sequence
<220> FEATURE:
<223> OTHER INFORMATION: hamster-actin-R primer

<400> SEQUENCE: 16
```

| | |
|---|---|
| agggaaatgg tgtgtgacat c | 21 |

```
<210> SEQ ID NO 17
<211> LENGTH: 23
<212> TYPE: DNA
<213> ORGANISM: Artificial Sequence
<220> FEATURE:
<223> OTHER INFORMATION: EGFP-F primer

<400> SEQUENCE: 17
agcagcacga cttcttcaag tcc                                               23

<210> SEQ ID NO 18
<211> LENGTH: 24
<212> TYPE: DNA
<213> ORGANISM: Artificial Sequence
<220> FEATURE:
<223> OTHER INFORMATION: EGFP-R primer

<400> SEQUENCE: 18
tgtagttgta ctccagcttg tgcc                                              24
```